(12) United States Patent
Uehara

(10) Patent No.: US 12,307,151 B2
(45) Date of Patent: May 20, 2025

(54) INFORMATION PROCESSING APPARATUS, INFORMATION PROCESSING METHOD, RADIATION IMAGING SYSTEM, AND STORAGE MEDIUM

(71) Applicant: CANON KABUSHIKI KAISHA, Tokyo (JP)

(72) Inventor: Keiko Uehara, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/534,329

(22) Filed: Dec. 8, 2023

(65) Prior Publication Data

US 2024/0201920 A1 Jun. 20, 2024

(30) Foreign Application Priority Data

Dec. 16, 2022 (JP) .................................. 2022-201211

(51) Int. Cl.
*G09G 5/00* (2006.01)
*G06F 3/14* (2006.01)

(52) U.S. Cl.
CPC ..................... *G06F 3/14* (2013.01)

(58) Field of Classification Search
CPC ....... G06F 3/14; G06F 3/147; G09G 2380/08; A61B 6/42; A61B 6/465; A61B 6/52; A61B 6/54; A61B 6/563; G16H 30/20
See application file for complete search history.

(56) References Cited

U.S. PATENT DOCUMENTS

| | | | | |
|---|---|---|---|---|
| 6,201,249 B1 * | 3/2001 | Yamayoshi | .......... | A61B 6/4494 250/370.11 |
| 10,485,505 B2 * | 11/2019 | Yamada | ................ | A61B 6/566 |
| 10,685,088 B2 * | 6/2020 | Ohashi | .................... | A61B 6/566 |
| 11,538,187 B2 * | 12/2022 | Arima | ...................... | G06T 7/80 |
| 11,540,802 B2 * | 1/2023 | Kim | ........................ | A61B 6/56 |
| 12,044,811 B2 * | 7/2024 | Kawai | .................... | G01N 23/04 |
| 12,059,287 B2 * | 8/2024 | Uehara | .................. | A61B 6/545 |
| 2005/0169425 A1 * | 8/2005 | Takasawa | .............. | A61B 6/547 378/97 |
| 2011/0311026 A1 * | 12/2011 | Lalena | ................... | G16H 40/63 378/98.5 |
| 2014/0112447 A1 * | 4/2014 | Semba | ................ | A61B 6/5241 378/91 |
| 2016/0133012 A1 * | 5/2016 | Miyazawa | ............ | G06T 7/0012 382/132 |
| 2017/0163869 A1 * | 6/2017 | Semba | .................... | A61B 6/465 |
| 2018/0125441 A1 * | 5/2018 | Arima | .................... | G16H 30/20 |
| 2022/0167935 A1 * | 6/2022 | Iwashita | .............. | A61B 6/4241 |
| 2022/0361832 A1 * | 11/2022 | Arai | ..................... | A61B 6/4441 |
| 2022/0370029 A1 * | 11/2022 | Taninai | ................ | A61B 6/5205 |

(Continued)

FOREIGN PATENT DOCUMENTS

JP 2019003230 A 1/2019

*Primary Examiner* — Joe H Cheng
(74) *Attorney, Agent, or Firm* — Canon U.S.A., Inc. IP Division

(57) ABSTRACT

An information processing apparatus includes an obtaining unit configured to obtain a processed image obtained by an external processing apparatus processing a radiation image from the external processing apparatus, and a control unit configured to perform control to, according to a display order of a plurality of processed images, display the plurality of processed images on a display unit.

16 Claims, 21 Drawing Sheets

(56) References Cited

U.S. PATENT DOCUMENTS

| | | | |
|---|---|---|---|
| 2023/0115379 A1* | 4/2023 | Koeda | A61B 6/486 382/128 |
| 2024/0201921 A1* | 6/2024 | Kawai | G06F 3/14 |
| 2024/0248220 A1* | 7/2024 | Yoshida | G01T 1/2992 |

* cited by examiner

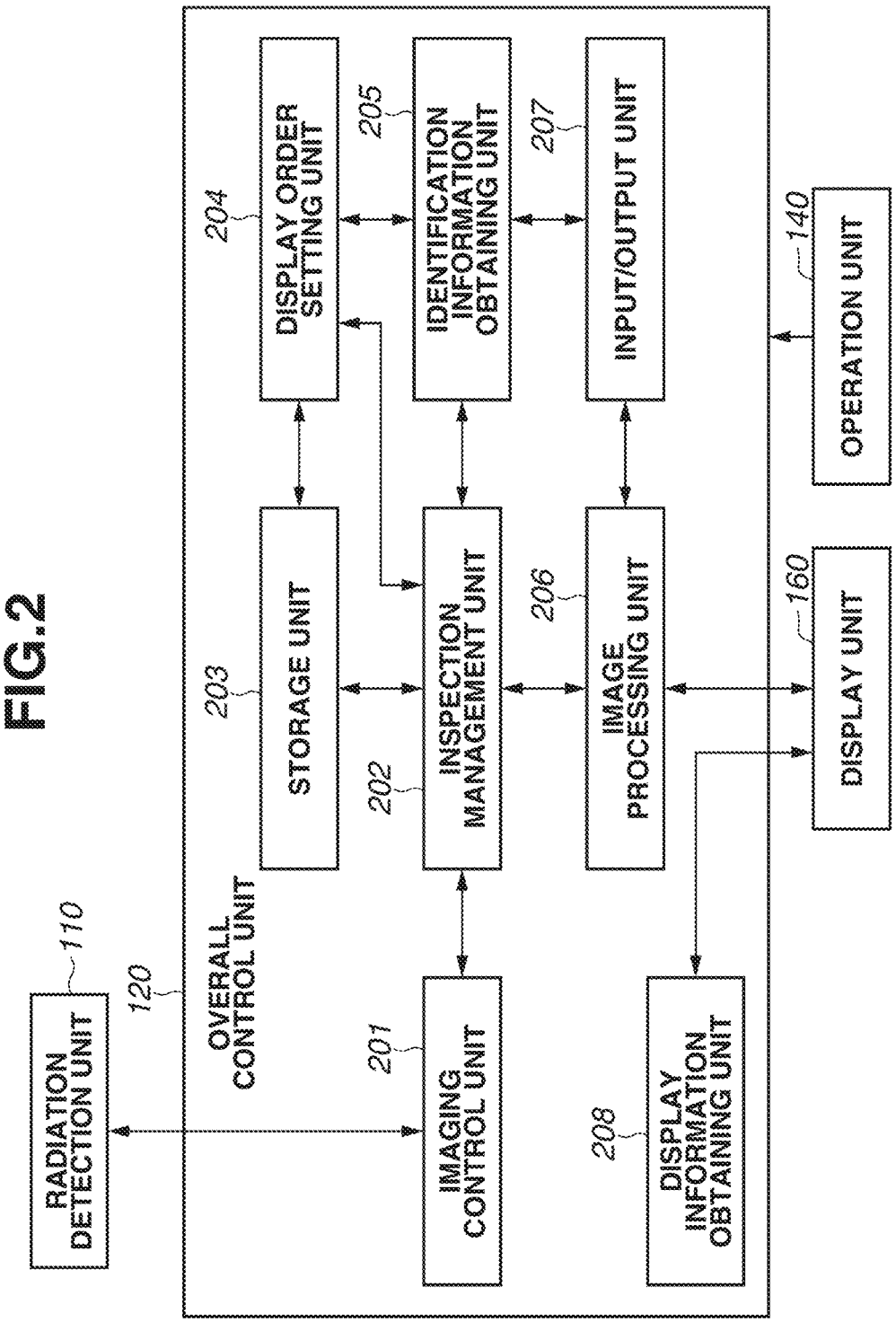

FIG.3A

| IMAGING METHOD ID | NAME | SENSOR | SBS SETTING | EXTERNAL PROCESSING REQUEST DESTINATION |
|---|---|---|---|---|
| 1 | CHEST FRONT | SENSOR A | ON | A, C |
| 2 | CHEST SIDE | SENSOR A | OFF | |
| 3 | ABDOMEN FRONT | SENSOR A | OFF | B |
| 4 | ABDOMEN SIDE | SENSOR A | ON | A |

FIG.3B

| EXTERNAL PROCESSING ID | PROCESSING REQUEST DESTINATION | PROCESSING CONTENT |
|---|---|---|
| 1 | SYSTEM A | FOR IMAGING SUPPORT |
| 2 | SYSTEM B | FOR IMAGING SUPPORT |
| 3 | SYSTEM C | FOR DIAGNOSIS SUPPORT |

FIG.4

| IMAGE ID | IMAGING METHOD ID | SOURCE | PROCESSING CONTENT | CONFIRMATION STATE |
|---|---|---|---|---|
| 1 | 1 | IMAGING APPARATUS | — | COMPLETED |
| 2 | 1 | SYSTEM A | FOR IMAGING SUPPORT | COMPLETED |
| 3 | 1 | SYSTEM C | FOR DIAGNOSIS SUPPORT | NOT YET |
| 4 | 2 | IMAGING APPARATUS | — | COMPLETED |
| 5 | 3 | IMAGING APPARATUS | — | COMPLETED |
| 6 | 3 | SYSTEM B | FOR IMAGING SUPPORT | NOT YET |
| 7 | 4 | IMAGING APPARATUS | — | COMPLETED |
| 8 | 4 | SYSTEM C | FOR DIAGNOSIS SUPPORT | COMPLETED |

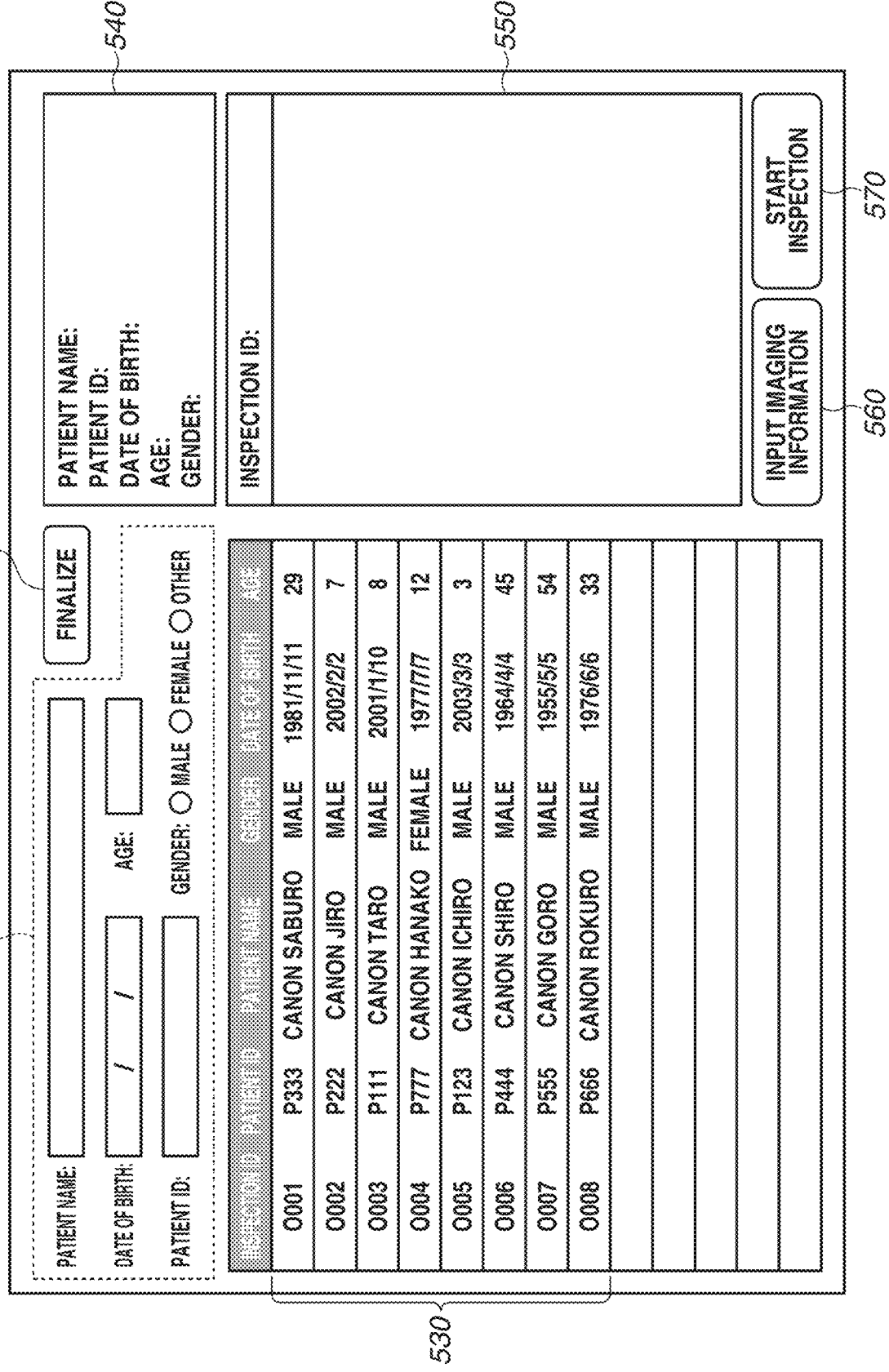

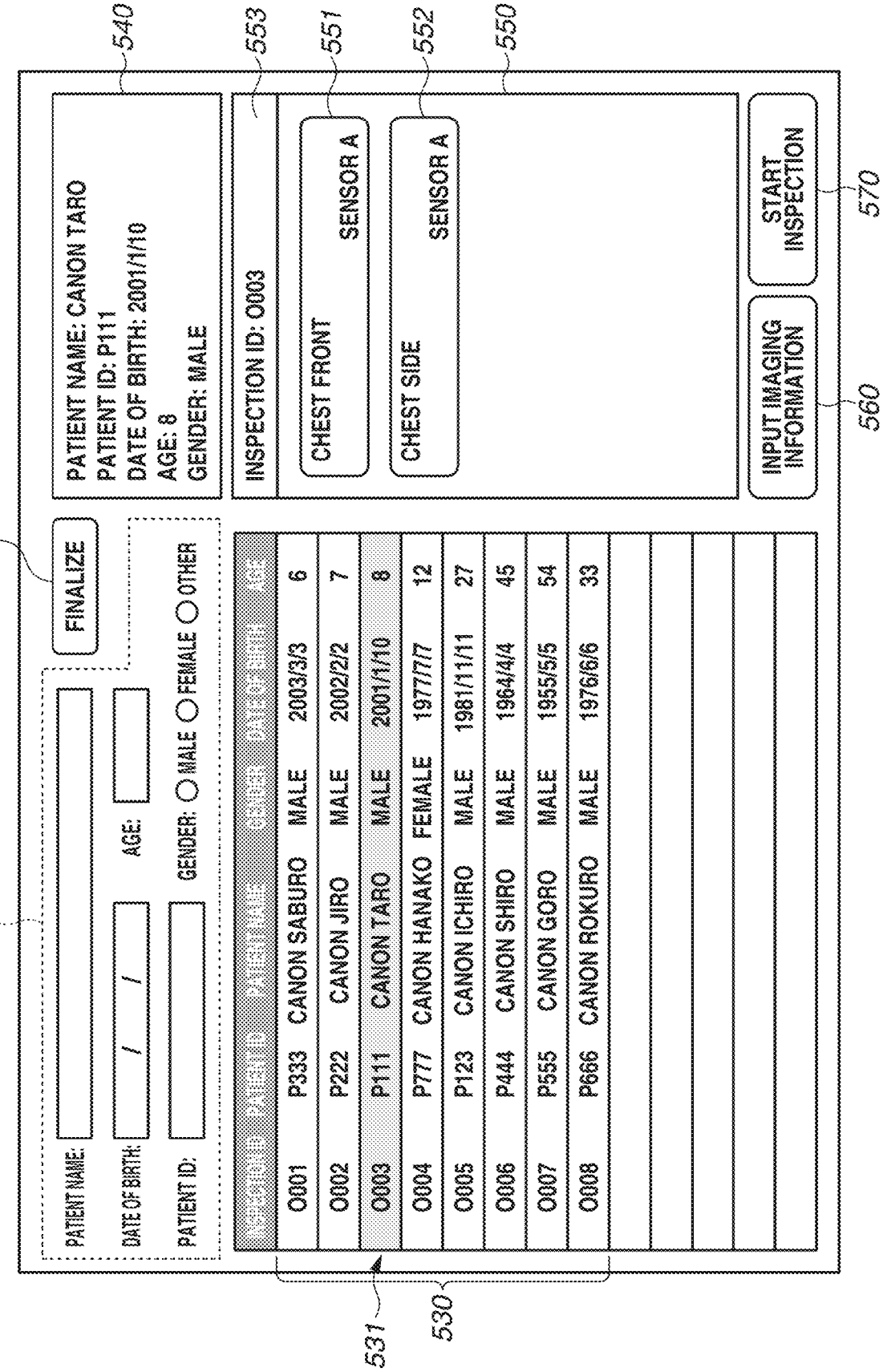

FIG.7

| IMAGE ID | SERIES ID | IMAGING METHOD ID | SOURCE | PROCESSING CONTENT |
|---|---|---|---|---|
| 1 | 1 | 1 | IMAGING APPARATUS | — |
| 2 | 1 | 1 | SYSTEM A | PROCESSING 2 |
| 3 | 1 | 1 | SYSTEM C | PROCESSING 3 |
| 4 | 1 | 1 | IMAGING APPARATUS | — |
| 5 | 2 | 2 | IMAGING APPARATUS | — |
| 6 | 3 | 3 | IMAGING APPARATUS | — |
| 7 | 3 | 3 | SYSTEM B | PROCESSING 1 |
| 8 | 4 | 1 | IMAGING APPARATUS | — |
| 9 | 4 | 1 | SYSTEM C | PROCESSING 3 |
| 10 | 4 | 1 | IMAGING APPARATUS | — |
| 11 | 4 | 1 | IMAGING APPARATUS | — |

FIG.8

| EXTERNAL PROCESSING ID | PROCESSING REQUEST DESTINATION | PROCESSING CONTENT | DISPLAY ORDER |
|---|---|---|---|
| 1 | SYSTEM A | PROCESSING 1 | 2 |
| 2 | SYSTEM A | PROCESSING 2 | 4 |
| 3 | SYSTEM B | PROCESSING 1 | 3 |
| 4 | SYSTEM C | PROCESSING 3 | 1 |

FIG.10

| IMAGING METHOD ID | NAME | SENSOR | PRIORITY EXTERNAL PROCESSING |
|---|---|---|---|
| 1 | CHEST FRONT | SENSOR A | A |
| 2 | CHEST SIDE | SENSOR A | |
| 3 | ABDOMEN FRONT | SENSOR A | B |
| 4 | ABDOMEN SIDE | SENSOR A | A |

FIG.13

| IMAGE ID | SERIES ID | IMAGING METHOD ID | SOURCE | PROCESSING CONTENT | OUTPUT |
|---|---|---|---|---|---|
| 1 | 1 | 1 | IMAGING APPARATUS | — | COMPLETED |
| 2 | 1 | 1 | SYSTEM A | PROCESSING 2 | — |
| 3 | 1 | 1 | SYSTEM C | PROCESSING 3 | — |
| 4 | 1 | 1 | IMAGING APPARATUS | — | |
| 5 | 2 | 2 | IMAGING APPARATUS | — | COMPLETED |
| 6 | 3 | 3 | IMAGING APPARATUS | — | COMPLETED |
| 7 | 3 | 3 | SYSTEM B | PROCESSING 1 | — |
| 8 | 4 | 1 | IMAGING APPARATUS | — | COMPLETED |
| 9 | 4 | 1 | SYSTEM C | PROCESSING 3 | — |
| 10 | 4 | 1 | IMAGING APPARATUS | — | COMPLETED |
| 11 | 4 | 1 | IMAGING APPARATUS | — | |

FIG.15

| IMAGE ID | SERIES ID | IMAGING METHOD ID | SOURCE | PROCESSING CONTENT | REJECTION (OR DELETION) |
|---|---|---|---|---|---|
| 1 | 1 | 1 | IMAGING APPARATUS | — | COMPLETED |
| 2 | 1 | 1 | SYSTEM A | PROCESSING 2 | |
| 3 | 1 | 1 | SYSTEM C | PROCESSING 3 | COMPLETED |
| 4 | 1 | 1 | IMAGING APPARATUS | — | |
| 5 | 2 | 2 | IMAGING APPARATUS | — | |
| 6 | 3 | 3 | IMAGING APPARATUS | — | |
| 7 | 3 | 3 | SYSTEM B | PROCESSING 1 | |
| 8 | 4 | 1 | IMAGING APPARATUS | — | |
| 9 | 4 | 1 | SYSTEM C | PROCESSING 3 | |
| 10 | 4 | 1 | IMAGING APPARATUS | — | |
| 11 | 4 | 1 | IMAGING APPARATUS | — | |

FIG.18

| IMAGE ID | SERIES ID | IMAGING METHOD ID | SOURCE | PROCESSING CONTENT | TRANSMISSION ID |
|---|---|---|---|---|---|
| 1 | 1 | 1 | IMAGING APPARATUS | — | — |
| 2 | 1 | 1 | SYSTEM A | PROCESSING 2 | 2 |
| 3 | 1 | 1 | SYSTEM C | PROCESSING 3 | 1 |
| 4 | 1 | 1 | IMAGING APPARATUS | — | — |
| 5 | 2 | 2 | IMAGING APPARATUS | — | — |
| 6 | 3 | 3 | IMAGING APPARATUS | — | — |
| 7 | 3 | 3 | SYSTEM B | PROCESSING 1 | 5 |
| 8 | 4 | 1 | IMAGING APPARATUS | — | — |
| 9 | 4 | 1 | SYSTEM C | PROCESSING 3 | 6 |
| 10 | 4 | 1 | IMAGING APPARATUS | — | — |
| 11 | 4 | 1 | IMAGING APPARATUS | — | — |

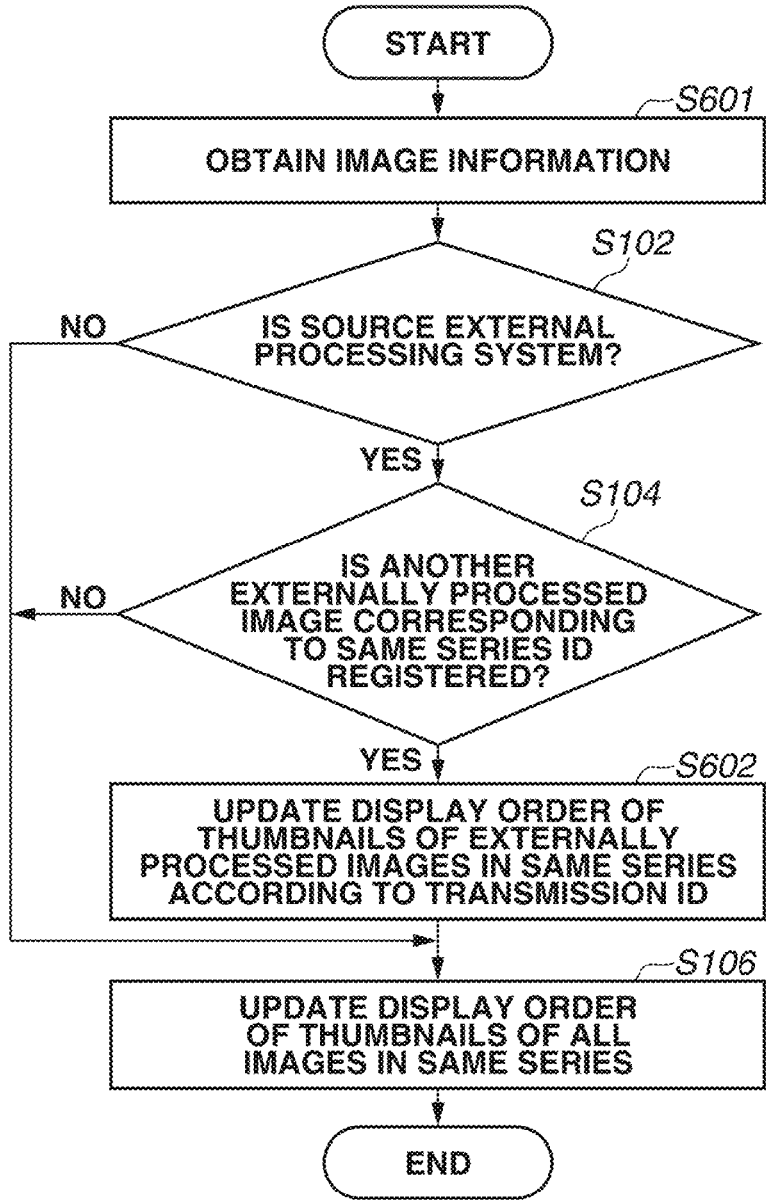

INFORMATION PROCESSING APPARATUS, INFORMATION PROCESSING METHOD, RADIATION IMAGING SYSTEM, AND STORAGE MEDIUM

This application claims the benefit of Japanese Patent Application No. 2022-201211, filed Dec. 16, 2022, which is hereby incorporated by reference herein in its entirety.

BACKGROUND OF THE DISCLOSURE

Field of the Disclosure

The present disclosure relates to an information processing apparatus, an information processing method, a radiation imaging system, and a storage medium.

Description of the Related Art

A radiation imaging apparatus and a radiation imaging system including the radiation imaging apparatus are known. The radiation imaging apparatus emits radiation to a subject, detects the intensity distribution of the radiation passing through the subject, and captures a radiation image of the subject. In an inspection using radiation (a radiation inspection), a doctor in each specialty typically sets inspection information including an imaging target part of a subject and an imaging method. Radiation imaging is then executed based on the set inspection information using the radiation imaging apparatus. Japanese Patent Application Laid-Open No. 2019-3230 discusses a medical system that manages a plurality of pieces of inspection information and displays a list screen that enables the grasp of the relationships between the pieces of inspection information according to an operation of a doctor.

In recent years, artificial intelligence (AI) technology advances for medical image diagnosis support. On the radiation imaging apparatus, an image processing system for diagnosis support can be mounted. Using an external image processing system outside the radiation imaging apparatus, it is possible to obtain support more useful for a user such as a doctor. In this case, the radiation imaging apparatus can cooperate with an external processing apparatus serving as the external image processing system to transmit and receive a radiation image as an original image and a processed image after the radiation image is processed to and from each other and can provide a processed image subjected to processing that is not mounted on the radiation imaging apparatus for a diagnosis.

In a case where externally processed images are generated by external processing apparatuses outside a radiation imaging apparatus processing a radiation image, the order of receiving the externally processed images from the external processing apparatuses by the radiation imaging apparatus may not be constant according to the types of the external processing apparatuses or the type of the processing content of each external processing apparatus. For example, in a case where a plurality of radiation images captured using two or more imaging methods is transmitted to the same external processing apparatus, the reception order of externally processed images corresponding to the radiation images may not match the transmission order of the radiation images. In such a case, when a plurality of externally processed images received from the external processing apparatus is displayed on a display unit, the externally processed images may not be displayed in the display order assumed by a user, and it may be difficult for the user to efficiently perform the work of confirming an externally processed image. At this time, the operability for the user may decrease, or an image may be incorrectly recognized.

SUMMARY OF THE DISCLOSURE

The present disclosure is directed to providing a mechanism in which a user can efficiently perform the work of confirming a processed image. Based on this, for example, a user can efficiently perform the work of confirming a processed image.

According to an aspect of the present disclosure, an information processing apparatus includes an obtaining unit configured to obtain a processed image obtained by an external processing apparatus processing a radiation image from the external processing apparatus, and a control unit configured to perform control to, according to a display order of a plurality of processed images, display the plurality of processed images on a display unit.

Further features of the present disclosure will become apparent from the following description of exemplary embodiments with reference to the attached drawings.

BRIEF DESCRIPTION OF THE DRAWINGS

FIG. 2 is a diagram illustrating the first exemplary embodiment of the present disclosure and illustrating an example of a schematic configuration of an overall control unit illustrated in FIG. 1.

FIGS. 3A and 3B are diagrams illustrating the first exemplary embodiment of the present disclosure and illustrating examples of an imaging method table and an external processing table stored in a storage unit illustrated in FIG. 2.

FIG. 4 is a diagram illustrating the first exemplary embodiment of the present disclosure and illustrating an example of an image table that stores image information regarding a radiation image obtained by a radiation imaging apparatus illustrated in FIG. 1 and an externally processed image obtained by each external processing apparatus illustrated in FIG. 1.

FIG. 5-1 is a diagram illustrating the first exemplary embodiment of the present disclosure and illustrating an example of a new inspection input screen displayed on a display unit illustrated in FIG. 1.

FIG. 5-2 is a diagram illustrating an example of a new inspection input screen displayed on the display unit illustrated in FIG. 1.

FIG. 5-3 is a diagram illustrating an example of an imaging information input screen displayed on the display unit illustrated in FIG. 1.

FIG. 7 is a diagram illustrating the first exemplary embodiment of the present disclosure and illustrating an example of an image table that stores image information regarding a radiation image obtained by the radiation imaging apparatus illustrated in FIG. 1 and an externally processed image obtained by each external processing apparatus illustrated in FIG. 1.

FIG. 8 is a diagram illustrating the first exemplary embodiment of the present disclosure and illustrating an example of an external processing table stored in the storage unit illustrated in FIG. 2.

FIG. 10 is a diagram illustrating a second exemplary embodiment of the present disclosure and illustrating an example of an imaging method table stored in the storage unit illustrated in FIG. 2.

FIG. 13 is a diagram illustrating the third exemplary embodiment of the present disclosure and illustrating an example of an image table that stores image information regarding a radiation image obtained by the radiation imaging apparatus illustrated in FIG. 1 and an externally processed image obtained by each external processing apparatus illustrated in FIG. 1.

FIG. 15 is a diagram illustrating a fourth exemplary embodiment of the present disclosure and illustrating an example of an image table that stores image information regarding a radiation image obtained by the radiation imaging apparatus illustrated in FIG. 1 and an externally processed image obtained by each external processing apparatus illustrated in FIG. 1.

FIG. 18 is a diagram illustrating a sixth exemplary embodiment of the present disclosure and illustrating an example of an image table that stores image information regarding a radiation image obtained by the radiation imaging apparatus illustrated in FIG. 1 and an externally processed image obtained by each external processing apparatus illustrated in FIG. 1.

FIG. 19 is a flowchart illustrating an example of a processing procedure in a control method for controlling a radiation imaging apparatus according to the sixth exemplary embodiment of the present disclosure.

DESCRIPTION OF THE EMBODIMENTS

Embodiments (exemplary embodiments) for carrying out the present disclosure will be described below with reference to the drawings.

A first exemplary embodiment will now be described.

Figure 1:
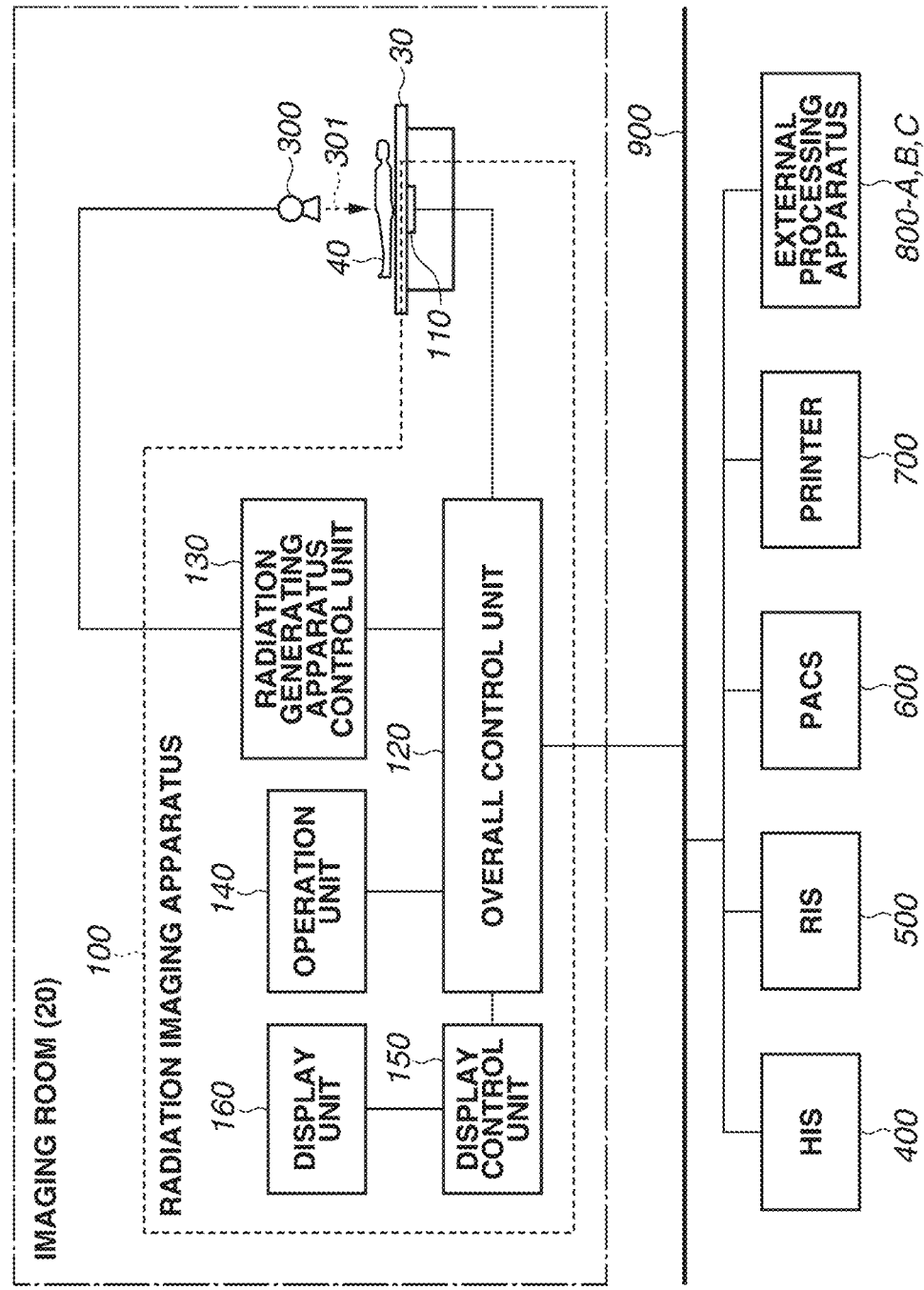
FIG. 1 is a diagram illustrating an example of a schematic configuration of a radiation imaging system according to a first exemplary embodiment of the present disclosure.

FIG. 1 is a diagram illustrating an example of a schematic configuration of a radiation imaging system 10 according to the first exemplary embodiment of the present disclosure. The radiation imaging system 10 includes a radiation imaging apparatus 100, a radiation generating apparatus 300, a hospital information system (HIS) 400, a radiology information system (RIS) 500, a picture archiving and communication system (PACS) 600, a printer 700, external processing apparatuses 800-A, 800-B, and 800-C, and a network 900. In an imaging room 20, the radiation imaging apparatus 100, the radiation generating apparatus 300, and an imaging table 30 are installed. The radiation imaging apparatus 100 includes a radiation detection unit 110, an overall control unit 120, a radiation generating apparatus control unit 130, an operation unit 140, a display control unit 150, and a display unit 160.

The radiation generating apparatus 300 emits radiation 301 toward a subject 40 placed on the imaging table 30 (e.g., a particular part of the subject 40) and the radiation detection unit 110 based on control of the radiation generating apparatus control unit 130. The radiation generating apparatus 300 functions as a radiation source that generates the radiation 301, and includes, for example, a radiation tubular lamp. The radiation generating apparatus 300 can emit the radiation 301 into a desired emission range. On an emission surface of the radiation generating apparatus 300, a diaphragm (not illustrated) for blocking the radiation 301 is installed. A user can adjust the emission range of the radiation 301 emitted from the radiation generating apparatus 300 by controlling the diaphragm.

The radiation imaging apparatus 100 is an apparatus for performing radiation imaging of the subject 40. The radiation imaging apparatus 100 is communicably connected to the HIS 400, the RIS 500, the PACS 600, the printer 700, and the external processing apparatuses 800-A to 800-E via the network 900.

The radiation detection unit 110 is a detection unit for detecting the radiation 301 that has passed through the subject 40 and generating a radiation image (radiation image data according to the radiation 301). Specifically, the radiation detection unit 110 detects the radiation 301 having passed through the subject 40 as an electric signal (a charge) corresponding to the amount of transmitted radiation. For example, the radiation detection unit 110 is composed of a direct conversion sensor made of amorphous selenium (a-Se) or the like that directly converts the radiation 301 into an electric signal (a charge) or an indirect-type sensor that uses a scintillator made of cesium iodide (CsI) and a photoelectric conversion element made of amorphous silicon (a-Si) and the like is used. The radiation detection unit 110 then performs analog-to-digital (A/D) conversion on the detected electric signal (charge) to generate radiation image data and store the radiation image data in a storage unit (not illustrated).

The radiation detection unit 110 can assign image information (e.g., an image identifier (ID), the imaging date and time, and the transfer status of the image data) to the radiation image data and transfer the image information with the radiation image data to the overall control unit 120.

The overall control unit 120 performs overall control of the operation of the radiation imaging apparatus 100 and also performs various processes based on, for example, an operation input on the operation unit 140. The overall control unit 120 is connected to the radiation detection unit 110 via, for example, a wireless local area network (LAN). The overall control unit 120 and the radiation detection unit 110 transmit and receive radiation image data and a control signal to and from each other. That is, radiation image data stored in the radiation detection unit 110 after radiation imaging is output (transferred) to the overall control unit 120 via the wireless LAN. The overall control unit 120 has an application function that operates on a computer. For example, the overall control unit 120 controls the operation of the radiation detection unit 110 and also outputs images including a radiation image to the display unit 160 or outputs a graphical user interface (GUI) to the display unit 160, via the display control unit 150.

The radiation generating apparatus control unit 130 sets imaging conditions for the radiation 301 in the radiation generating apparatus 300 and controls the radiation generating apparatus 300 based on control of the overall control unit 120.

The operation unit 140 inputs, for example, an operation input from the user to the overall control unit 120.

The operation unit 140 is composed of, for example, a mouse and an operation button. The operation unit 140 inputs various instructions from the user to the overall control unit 120.

The display control unit 150 controls the display unit 160 based on control of the overall control unit 120.

The display unit 160 displays various images and various pieces of information, based on control of the display control unit 150. The display unit 160 is achieved by, for example, a liquid crystal display. The display unit 160 displays various images and various pieces of information to the user (e.g., a photographer or a doctor). The display unit 160 and the operation unit 140 can be achieved as a touch panel in which the display unit 160 and the operation unit 140 are integrated together.

The HIS 400 is a hospital information system including a server for managing the progress of an inspection and accounting information. In a case where radiation imaging is performed, the user inputs an inspection instruction through a terminal (input unit) of the HIS 400. The HIS 400 then transmits request information to the radiology department of the hospital as the request destination of the radiation imaging. This request information is referred to as an "inspection order". The inspection order includes the department name of the request source, an inspection ID, an inspection item, and patient information as an example of subject information regarding the subject 40. Execution information (an image ID and the imaging date and time) regarding an inspection executed by the radiation imaging apparatus 100 is transmitted to the HIS 400. The execution information transmitted to the HIS 400 is used to manage the progress of the inspection and is also used in an accounting process after the inspection.

The RIS 500 is a radiology information system for transmitting, for example, an inspection order to the radiation imaging apparatus 100. When the RIS 500 receives an inspection order, the radiology department of the hospital serving as the request destination of radiation imaging adds imaging information regarding the radiation imaging (e.g., imaging target part information, imaging direction information, and manipulation information) as an imaging protocol to the inspection order and transmits the inspection order to the radiation imaging apparatus 100. The radiation imaging apparatus 100 then executes the radiation imaging according to the received inspection order. The radiation imaging apparatus 100 obtains a radiation image of the subject 40 through the radiation imaging, generates inspection information in which the radiation image and the inspection order are associated together, and outputs the inspection information with the radiation image.

The PACS 600 is an image saving communication system for managing various images including a radiation image. For example, the PACS 600 is a server mainly intended to image management. Using a high-definition monitor connected to the PACS 600, the work of examining radiation images, detailed post-processing, and diagnosis work are executed. As described above, a radiation image obtained by the radiation imaging apparatus 100 is transmitted to the PACS 600.

The printer 700 performs print output of various images including a radiation image and various pieces of information.

Each external processing apparatus 800 generates an externally processed image by processing (performing image processing on) a radiation image obtained by the radiation imaging apparatus 100 performing radiation imaging. Each external processing apparatus 800 is an external image processing system outside the radiation imaging apparatus 100. The external processing apparatus 800 then transmits the generated externally processed image to the radiation imaging apparatus 100 (and further, the PACS 600). The radiation imaging apparatus 100 then presents the externally processed image received from the external processing apparatus 800 with the original radiation image and provides processing that is not mounted on the radiation imaging apparatus 100. In the present exemplary embodiment, the external processing apparatus 800 performs diagnosis support processing and imaging support processing using AI technology. In the example illustrated in FIG. 1, three external processing apparatuses 800-A, 800-B, and 800-C are provided as external processing apparatuses 800. In the following description, the external processing apparatus 800-A is referred to as an "external processing system A", the external processing apparatus 800-B is referred to as an "external processing system B", and the external processing apparatus 800-C is referred to as an "external processing system C", where necessary. In the following description, descriptions common to the external processing apparatuses 800-A, 800-B, and 800-C are given by referring to the external processing apparatuses 800-A, 800-B, and 800-C simply as an "external processing apparatus 800", where necessary.

The network 900 connects the radiation imaging apparatus 100, the HIS 400, the RIS 500, the PACS 600, the printer 700, and the external processing apparatuses 800-A, 800-B, and 800-C so that these apparatuses can communicate with each other. The network 900 is composed of, for example, a LAN or a wide area network (WAN).

Each of the apparatuses 100 and 300 to 800 includes one or more computers. In each computer, for example, a main control unit such as a central processing unit (CPU) and storage units such as a read-only memory (ROM) and a random-access memory (RAM) are provided. In each computer, a communication unit such as a network card and input/output units such as a keyboard, a display, and a touch panel can also be provided. These component units are electrically connected together by a bus and controlled by the main control unit executing programs stored in the storage units.

The configuration illustrated in FIG. 1 is merely an example and can be appropriately changed. For example, the various apparatuses (400 to 800) are connected to the radiation imaging apparatus 100 via the network 900 so that the various apparatuses (400 to 800) can communicate with the radiation imaging apparatus 100 in FIG. 1. However, the present exemplary embodiment is not limited to the configuration illustrated in FIG. 1. For example, a configuration can be employed in which a radiation image obtained by the radiation imaging apparatus 100 is stored in a portable storage medium, such as a digital versatile disc (DVD) and input to the various apparatuses (400 to 800) via the portable storage medium. The network 900 can be composed of a wired network, or a part of the network 900 can be composed of a wireless signal transmission path.

FIG. 2 is a diagram illustrating the first exemplary embodiment of the present disclosure and illustrating an example of the schematic configuration of the overall control unit 120 illustrated in FIG. 1. In FIG. 2, components similar to the components illustrated in FIG. 1 are designated by the same signs, and are not described in detail.

The overall control unit 120 includes, as illustrated in FIG. 2, an imaging control unit 201, an inspection management unit 202, a storage unit 203, a display order setting unit 204, an identification information obtaining unit 205, an image processing unit 206, an input/output unit 207, and a display information obtaining unit 208.

The imaging control unit 201 controls radiation imaging in the radiation detection unit 110. For example, the imaging control unit 201 transmits to the radiation detection unit 110 a transfer request signal requesting the radiation detection unit 110 to transfer a radiation image, and receives the radiation image from the radiation detection unit 110. The imaging control unit 201 manages the received radiation image with radiation detection unit information regarding the radiation detection unit 110. The radiation image is further associated with inspection information and an imaging protocol managed by the inspection management unit 202.

The inspection management unit 202 manages inspection information in which a radiation image and an inspection order are associated together. Specifically, the inspection management unit 202 manages an imaging protocol in which an imaging method, imaging conditions, and image processing conditions associated with the inspection order are defined. For example, in a case where the radiation imaging apparatus 100 generates inspection information, the inspection management unit 202 can also associate subject information and an imaging protocol input from the operation unit 140 and create new inspection information. In contrast, in a case where an inspection order is transmitted from the RIS 500, the inspection management unit 202 extracts an imaging protocol stored in the storage unit 203, by using protocol information regarding an imaging protocol associated with the inspection order received from the RIS 500. The inspection management unit 202 then associates the extracted imaging protocol and the inspection order and creates new inspection information. The newly created inspection information is stored in the storage unit 203. The inspection management unit 202 also associates a radiation image obtained by the radiation imaging apparatus 100 and an externally processed image obtained by each external processing apparatus 800, by using identification information (e.g., a series ID in FIG. 7), and stores the radiation image and the externally processed image in the storage unit 203.

The storage unit 203 stores various images including a radiation image generated by the radiation detection unit 110 and various pieces of information, such as an inspection order, an imaging protocol, and an imaging method. The storage unit 203 also stores programs executed when the overall control unit 120 performs various types of control and various processes. The storage unit 203 also stores inspection information, an imaging protocol, and an imaging method associated with an inspection order by the inspection management unit 202, a radiation image output from the radiation detection unit 110, an externally processed image and identification information input from the input/output unit 207, and various pieces of information required to manage an inspection. For example, the storage unit 203 also stores, for example, setting information for setting whether each of the registered external processing apparatuses 800-A, 800-B, and 800-C is an external processing apparatus 800 (an external processing system) that outputs a diagnosis support image.

The identification information obtaining unit 205 obtains identification information regarding an externally processed image input from the input/output unit 207.

Based on information obtained from the identification information obtaining unit 205 and the storage unit 203, the display order setting unit 204 sets the display order of displaying on the display unit 160 a radiation image and an externally processed image obtained by each external processing apparatus 800 performing image processing. For example, the display order setting unit 204 sets the display order of thumbnails of a plurality of externally processed images generated by the external processing apparatuses 800, based on image information, information regarding an imaging protocol, and information regarding each external processing apparatus 800 that are stored in the storage unit 203. For example, the inspection management unit 202 then changes the display order of the thumbnails of the plurality of externally processed images generated by the external processing apparatuses 800, based on the result of the display order setting unit 204 setting the display order. Regarding this process of changing the display order, the image information stored in the storage unit 203 may be rewritten, and the inspection management unit 202 may read the image information and change the display order. Alternatively, based on identification information obtained by the identification information obtaining unit 205, the display order setting unit 204 may set and store the display order of the thumbnails of the plurality of externally processed images generated by the external processing apparatuses 800 at the timing when the identification information is stored in the storage unit 203.

The image processing unit 206 performs image processing on a radiation image obtained by the radiation detection unit 110. The image processing unit 206 performs the image processing on the radiation image by using an imaging protocol and image information obtained by the imaging control unit 201. The radiation image subjected to the image processing is displayed on the display unit 160 and/or output from the input/output unit 207 to each external processing apparatus 800. The image processing unit 206 performs image processing for adjusting the image itself, such as adjusting the luminance and the contrast of the image. The image processing unit 206 can also perform an editing process, such as clipping and annotation, on the adjusted radiation image.

The input/output unit 207 outputs or inputs various images and various pieces of information to and from an external apparatus. For example, the input/output unit 207 receives the input of an inspection order from the RIS 500 and the input of an externally processed image from each external processing apparatus 800. For example, the input/output unit 207 also outputs a radiation image to an external apparatus, such as the PACS 600, the printer 700, or each external processing apparatus 800, and outputs inspection execution information to the HIS 400.

The display information obtaining unit 208 obtains information about whether the externally processed image has once been displayed on the display unit 160.

FIGS. 3A and 3B are diagrams illustrating the first exemplary embodiment of the present disclosure and illustrating examples of an imaging method table and an external processing table stored in the storage unit 203 illustrated in FIG. 2.

Specifically, FIG. 3A is a diagram illustrating an example of the imaging method table stored in the storage unit 203 illustrated in FIG. 2. The imaging method table illustrated in FIG. 3A is a table that stores, with respect to each imaging method, settings, such as an imaging method ID, the name of the imaging, a sensor type of the radiation detection unit 110 used in the imaging, a side-by-side display setting (an SBS setting), and an external processing request destination. The side-by-side display setting (the SBS setting) is a setting for displaying a plurality of images side by side in a single image display area. In the external processing request destination, "A" indicates the external processing apparatus 800-A (the external processing system A), "B" indicates the external processing apparatus 800-B (the external processing system B), and "C" indicates the external processing apparatus 800-C (the external processing system C).

FIG. 3B is a diagram illustrating an example of the external processing table stored in the storage unit 203 illustrated in FIG. 2. The external processing table illustrated in FIG. 3B is a table that stores, with respect to each external processing system, settings, such as an external processing ID, an external processing system as a processing request destination, and information indicating whether the external processing system as the processing request destination is for imaging support or for diagnosis support. For example, in the imaging of the abdomen front corresponding to the imaging method ID "3", the external processing request destination is the external processing apparatus 800-B (the external processing system B) based on FIG. 3A, and a captured radiation image is transmitted to the external processing system B for imaging support based on FIG. 3B.

FIG. 4 is a diagram illustrating the first exemplary embodiment of the present disclosure and illustrating an example of an image table that stores image information regarding a radiation image obtained by the radiation imaging apparatus 100 illustrated in FIG. 1 and an externally processed image obtained by each external processing apparatus 800 illustrated in FIG. 1. The image table illustrated in FIG. 4 is a table that stores, with respect to each image, an image ID, an imaging method ID, a source having obtained the image, a processing content as information indicating whether an external processing system indicated by the source is for imaging support or for diagnosis support, and a confirmation state of the image. In the confirmation state of the image in the image table illustrated in FIG. 4, the confirmation of the image is completed by displaying the image in an image display area 610 in FIG. 6.

In line with the flow of an inspection of the subject 40 by the radiation imaging system 10 illustrated in FIG. 1, a processing procedure for capturing a radiation image will be described.

According to a written inspection request or an inspection request from the RIS 500, patient information as an example of subject information regarding the subject 40 and inspection information are firstly input through the operation unit 140 of the radiation imaging apparatus 100. The patient information includes a patient name and a patient ID. The inspection information includes imaging information defining the content of imaging to be executed on the patient.

Figures 3, 5:
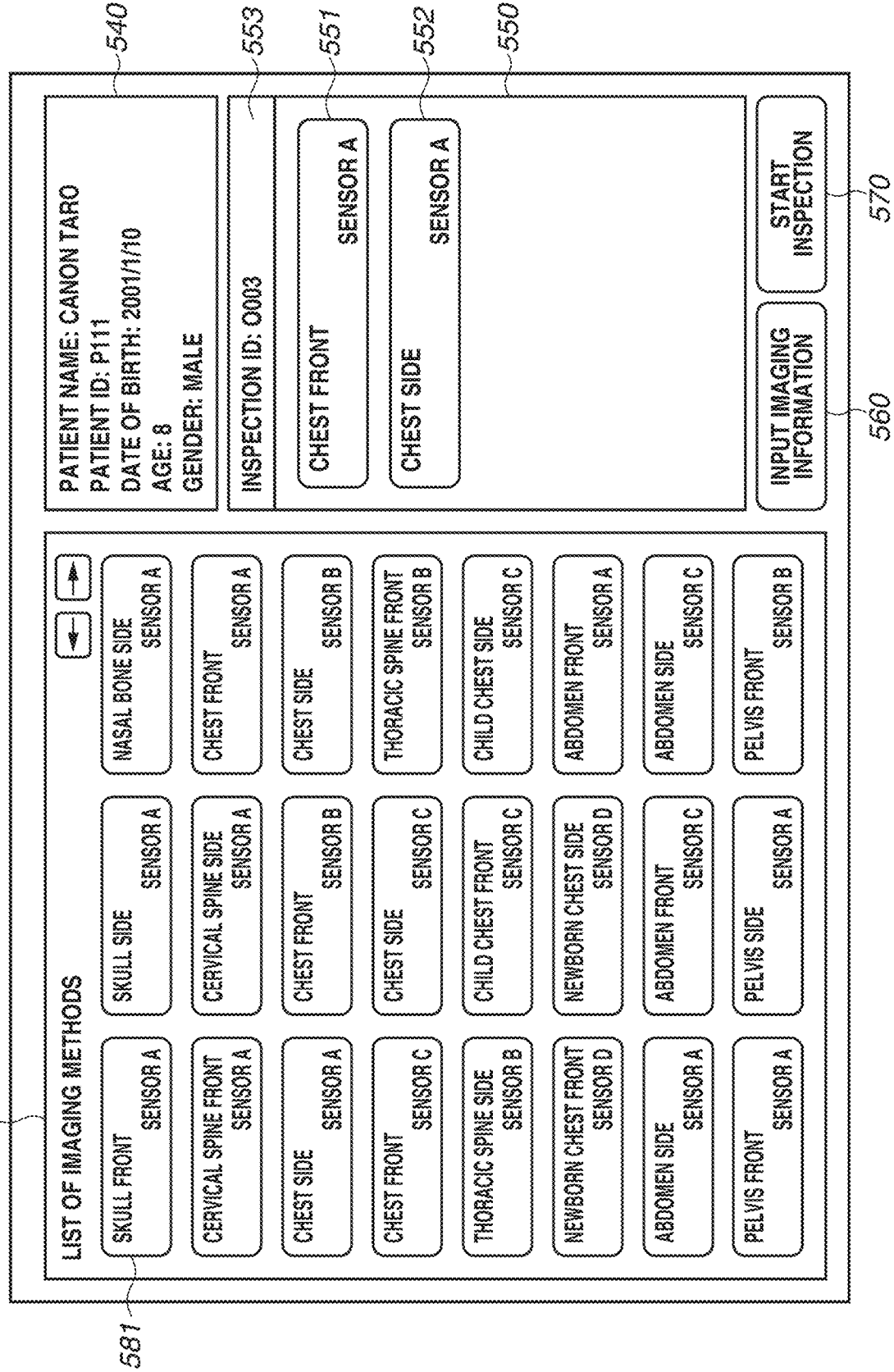

The radiation imaging apparatus 100 then displays a new inspection input screen on the display unit 160 based on control of the display control unit 150. FIGS. 5-1 and 5-2 are diagrams illustrating examples of the new inspection input screen displayed on the display unit 160 illustrated in FIG. 1. The new inspection input screen illustrated in FIG. 5-1 includes a patient information input area 510, a patient information finalization button 520, a requested inspection list 530, a patient information display area 540, an imaging information display area 550, an "input imaging information" button 560, and a "start inspection" button 570. In the requested inspection list 530 illustrated in FIG. 5-1, inspections received from the RIS 500 are arranged and displayed in a list.

If a single inspection 531 illustrated in FIG. 5-2 is selected from the requested inspection list 530 illustrated in FIG. 5-1, patient information (e.g., a patient ID, a patient name, and the date of birth) corresponding to the selected inspection 531 is then displayed in the patient information display area 540 as illustrated in FIG. 5-2. In the imaging information display area 550, an inspection ID corresponding to the selected inspection 531 is displayed in an inspection ID display area 553 as illustrated in FIG. 5-2. Further, in the imaging information display area 550, a "chest front" button 551 and a "chest side" button 552 as imaging method buttons corresponding to imaging information regarding the inspection ID are displayed in an area immediately below the inspection ID display area 553. The imaging information is received from the RIS 500.

FIG. 5-3 is a diagram illustrating the first exemplary embodiment of the present disclosure and illustrating an example of an imaging information input screen displayed on the display unit 160 illustrated in FIG. 1. The imaging information input screen illustrated in FIG. 5-3 is a screen displayed on the display unit 160 by the user pressing the "input imaging information" button 560 illustrated in FIG. 5-2 or the like. In FIG. 5-3, components similar to the components illustrated in FIGS. 5-1 and 5-2 are designated by the same signs, and are not described in detail. If the "input imaging information" button 560 illustrated in FIG. 5-2 is pressed, then as illustrated in FIG. 5-3, the display unit 160 displays a list of imaging methods in an imaging information input area 580, and the user can also add an imaging method. In the example illustrated in FIG. 5-3, a plurality of imaging method selection buttons 581 is displayed in the imaging information input area 580, and the user can add an imaging method by selecting any of the imaging method selection buttons 581. The added imaging method is displayed alongside the "chest front" button 551 and the "chest side" button 552 in the imaging information display area 550. Each imaging method is associated with an imaging method ID. If the user confirms the patient information and the imaging information and then presses the "start inspection" button 570, an inspection to be executed is finalized.

Figure 6:
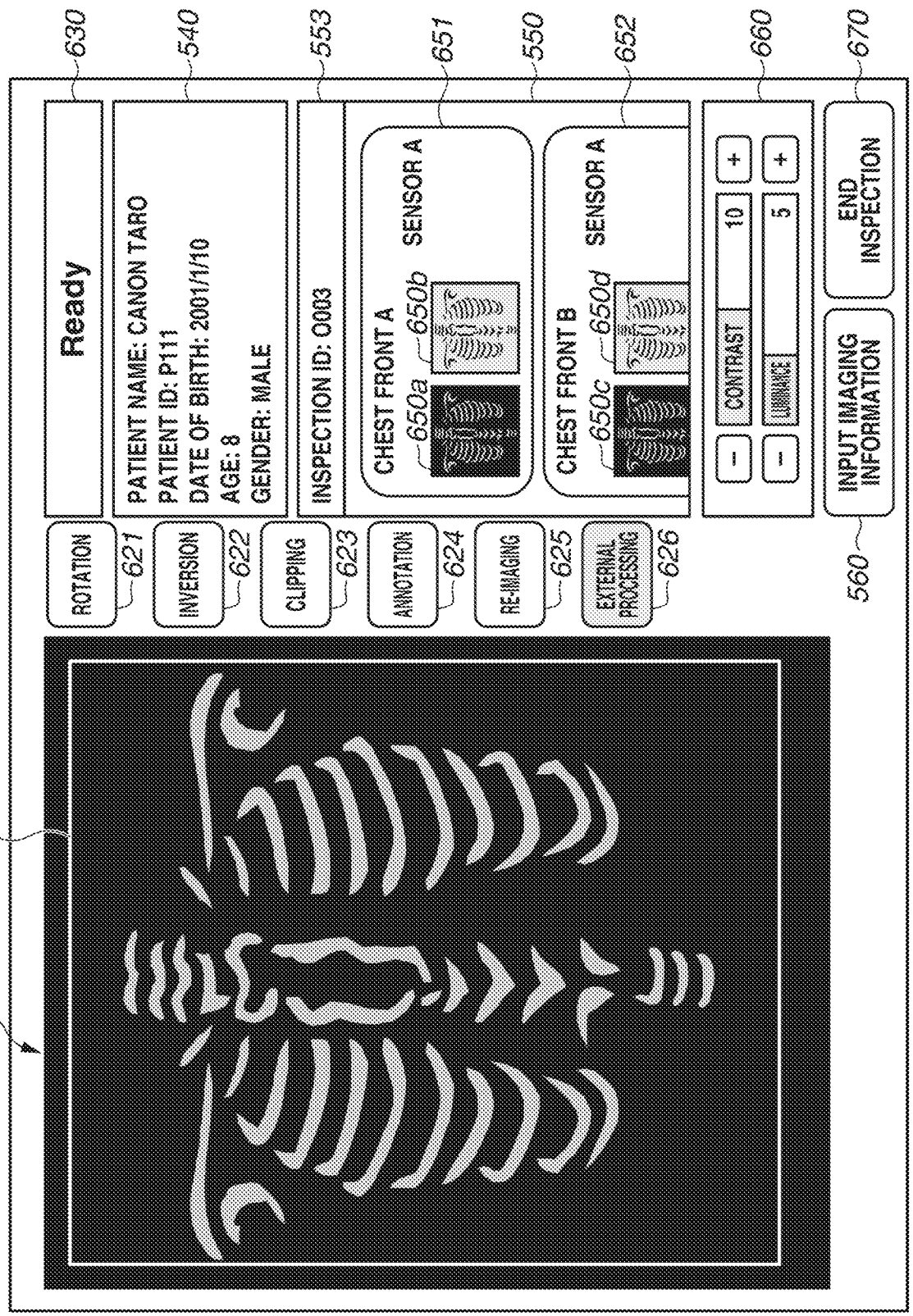
FIG. 6 is a diagram illustrating the first exemplary embodiment of the present disclosure and illustrating an example of an imaging screen displayed on the display unit illustrated in FIG. 1.

FIG. 6 is a diagram illustrating the first exemplary embodiment of the present disclosure and illustrating an example of an imaging screen displayed on the display unit 160 illustrated in FIG. 1. The imaging screen illustrated in FIG. 6 is a screen displayed on the display unit 160 by the user pressing the "start inspection" button 570 illustrated in FIG. 5-3 and the like, and is a screen used when radiation imaging of the subject 40 is performed. In FIG. 6, components similar to the components illustrated in FIGS. 5-1 to 5-3 are designated by the same signs, and are not described in detail.

On the imaging screen illustrated in FIG. 6, an image display area 610 and various buttons 621 to 626 are provided by replacing the patient information input area 510, the patient information finalization button 520, and the requested inspection list 530 on the new inspection input screen illustrated in FIG. 5-2. For example, the various buttons 621 to 626 illustrated in FIG. 6 are instruction buttons for an image displayed in the image display area 610. Specifically, a "rotation" button 621, an "inversion" button 622, a "clipping" button 623, an "annotation" button 624, a "re-imaging" button 625, and an "external processing" button 626 are provided as illustrated in FIG. 6.

On the imaging screen illustrated in FIG. 6, a message area 630 and an image processing setting area 660 are also added to the new inspection input screen illustrated in FIG. 5-2. On the imaging screen illustrated in FIG. 6, an "end inspection" button 670 is provided by replacing the "start inspection" button 570 on the new inspection input screen illustrated in FIG. 5-2. Further, on the imaging screen illustrated in FIG. 6, a "chest front A" button 651 including thumbnails 650*a* and 650*b* and a "chest front B" button 652 including thumbnails 650*c* and 650*d* are displayed in the imaging information display area 550. The thumbnail 650*a* is a thumbnail of a radiation image of a chest front A generated by the radiation imaging apparatus 100. The thumbnail 650*b* is a thumbnail of an externally processed image obtained by an external processing apparatus 800 processing the radiation image of the chest front A. The thumbnail 650*c* is a thumbnail of a radiation image of a chest front B generated by the radiation imaging apparatus 100. The thumbnail 650*d* is a thumbnail of an externally processed image obtained by an external processing apparatus 800 processing the radiation image of the chest front B.

Specifically, if the imaging screen illustrated in FIG. 6 is displayed on the display unit 160, the "chest front A" button 651 disposed at the top of the imaging information display area 550 is in a selected state by default. Accordingly, the overall control unit 120 of the radiation imaging apparatus 100 transmits imaging conditions (e.g., a tube voltage, a tube current, and an emission time) set corresponding to the "chest front A" button 651 (an imaging method) to the radiation generating apparatus control unit 130. The overall control unit 120 also controls the radiation detection unit 110 to be prepared for the radiation imaging of the subject 40 according to the imaging conditions. When the radiation imaging apparatus 100 is prepared for the radiation imaging of the subject 40, the overall control unit 120 causes the state of the radiation imaging apparatus 100 to transition to the state where imaging can be performed. At this time, a "Ready" message indicating the state where imaging can be performed is displayed in the message area 630 in the imaging screen illustrated in FIG. 6.

The user then checks the imaging method, sets the radiation imaging, and positions the patient as the subject 40. When a series of imaging preparations is completed, the user confirms with reference to the message area 630 that the radiation imaging apparatus 100 is in the state where imaging can be performed. Then, the user presses a radiation emission switch (not illustrated). As a result, the radiation generating apparatus 300 emits the radiation 301 toward a particular part of the patient as the subject 40, and the radiation detection unit 110 detects the radiation 301 having passed through the subject 40 and generates a radiation image of the subject 40.

When the radiation imaging of the subject 40 is completed, the overall control unit 120 of the radiation imaging apparatus 100 obtains the radiation image from the radiation detection unit 110 and also performs image processing on the obtained radiation image based on predetermined image processing conditions. The predetermined image processing conditions are defined in advance corresponding to the imaging method. When the image processing is completed, the radiation imaging apparatus 100 displays the radiation image subjected to the image processing in the image display area 610 illustrated in FIG. 6. The overall control unit 120 of the radiation imaging apparatus 100 also generates the thumbnail 650*a* of the radiation image generated by the radiation imaging apparatus 100 within the "chest front A" button 651.

If the user wants to change the contrast or the luminance of the radiation image displayed in the image display area 610 in FIG. 6, the user changes the contrast or the luminance by operating a "contrast" button or a "luminance" button provided in the image processing setting area 660.

If the user wants to change a clipping area of the radiation image displayed in the image display area 610 in FIG. 6, the user changes the clipping area to a desired clipping area by operating the "clipping" button 623 and a clipping frame 611. To assign a character string as diagnosis information, the user assigns a character string as indicated by an annotation on top of the image by operating the "annotation" button 624.

If the direction of the radiation image displayed in the image display area 610 in FIG. 6 is not suitable for a diagnosis, the user geometrically transforms the radiation image using the "rotation" button 621 or the "inversion" button 622 or the like. As described above, the user can execute additional image editing on the radiation image displayed in the image display area 610.

If the user wants to use image processing in the external processing apparatuses 800, the user presses the "external processing" button 626. In the imaging method table illustrated in FIG. 3A, whether to enable external processing by the external processing apparatuses 800 (a blank indicates that the external processing is not enabled) is set in advance in the external processing request destination. Further, if the external processing is enabled, an external processing apparatus 800 as the external processing request destination is set in advance.

In the external processing table illustrated in FIG. 3B, the processing content (for imaging support or for diagnosis support) of the external processing apparatus 800 as the external processing request destination is set in the processing content.

For example, if an image in the "chest front A" button 651 is displayed in the image display area 610, the "external processing" button 626 is enabled according to the setting of whether to enable external processing by an imaging method corresponding to the "chest front A" button 651. If the user presses the "external processing" button 626, the radiation imaging apparatus 100 transmits a radiation image displayed in the image display area 610 to an external processing apparatus 800. The external processing apparatus 800 as the transmission destination is determined according to the external processing request destination set for the imaging method corresponding to the "chest front A" button 651. For example, in the imaging of the chest front corresponding to the "chest front A" button 651, the radiation image is transmitted to the external processing apparatuses 800-A and 800-C according to the external processing request destination in the imaging method table illustrated in FIG. 3A. To the radiation image to be transmitted, for example, the image ID illustrated in FIG. 4 is also added to a header portion of the radiation image to identify the radiation image itself. In an operation where image processing by the external processing apparatuses 800 is always used, an embodiment may be employed in which, using the generation of a radiation image according to radiation imaging as a trigger, the radiation image is transmitted without pressing the "external processing" button 626.

An inspection order received from the RIS 500 by the radiation imaging apparatus 100 includes imaging information. A configuration can be employed in which the HIS 400 or the RIS 500 requests the generation of an externally processed image by external processing by specifying an imaging method for which external processing is set to enabled.

If the radiation imaging apparatus 100 receives an externally processed image from the external processing apparatus 800, the radiation imaging apparatus 100 identifies an imaging method ID, based on the image ID in FIG. 4 having been assigned to the radiation image when the radiation image is transmitted to the external processing apparatus 800. The radiation imaging apparatus 100 uses the identified imaging method ID, and then associates the radiation image transmitted to the external processing apparatus 800 and the externally processed image received from the external processing apparatus 800. The association can be made by receiving information regarding the externally processed image through communication different from that for the reception of the externally processed image. For example, in the case of the imaging of the chest front A, an externally processed image associated with the radiation image is displayed as the thumbnail 650b of the externally processed image within the "chest front A" button 651. Thereafter, if the user presses the thumbnail 650b, the externally processed image of the chest front A is displayed in the image display area 610 in FIG. 6.

The user repeats the above procedure, thereby executing the radiation imaging using all imaging methods in the imaging information display area 550. Then, if all the radiation imaging is completed, the user presses the "end inspection" button 670 illustrated in FIG. 6. Consequently, a series of inspection processes ends. The overall control unit 120 of the radiation imaging apparatus 100 assigns, to an image, information such as the inspection information and the imaging conditions regarding the image as additional information, and then, outputs the image to the PACS 600, the printer 700, or the ROM of the radiation imaging apparatus 100, for example. The overall control unit 120 of the radiation imaging apparatus 100 transmits, to the HIS 400, inspection execution information for notifying the HIS 400 that the inspection ends. At this time, the overall control unit 120 includes the identifier of an externally processed image received before the end of the inspection as an object in the inspection in the inspection execution information.

Then, the radiation imaging apparatus 100 displays the new inspection input screen illustrated in FIG. 5-1 on the display unit 160 again.

FIG. 7 is a diagram illustrating the first exemplary embodiment of the present disclosure and illustrating an example of an image table that stores image information regarding a radiation image obtained by the radiation imaging apparatus 100 illustrated in FIG. 1 and an externally processed image obtained by each external processing apparatus 800 illustrated in FIG. 1. The image table illustrated in FIG. 7 is stored in the storage unit 203. The image table illustrated in FIG. 7 is a table that stores, with respect to each image, an image ID, a series ID, an imaging method ID, a source having obtained the image, and a processing content of an external processing system indicated by the source. In the image table illustrated in FIG. 7, the imaging method ID is an ID assigned with respect to, for example, each of the types of the imaging method selection buttons 581 displayed in the imaging method input area 580 illustrated in FIG. 5-3. In the image table illustrated in FIG. 7, the series ID is, for example, an ID assigned with respect to each of the "chest front A" button 651 and the "chest front B" button 652 displayed in the imaging information display area 550 illustrated in FIG. 6. That is, as the series ID, different IDs are assigned to the "chest front A" button 651 and the "chest front B" button 652 illustrated in FIG. 6, for example. In the present exemplary embodiment, the same series includes a group of images related to each other (having certain features in common). For example, a series can be optionally set by the user. The reason is as follows why the image IDs "1" to "4" and the image IDs "8" to "11" in FIG. 7 correspond to the same imaging method ID ("1"), but correspond to different series IDs ("1" and "4"). For example, if there is a plurality of images obtained by an imaging method "chest front: sensor A", the same imaging method ID is assigned to the plurality of images based on FIG. 5-3, whereas different series ID are assigned between "chest front A: sensor A" and "chest front B: sensor A" based on FIG. 6.

FIG. 8 is a diagram illustrating the first exemplary embodiment of the present disclosure and illustrating an example of an external processing table stored in the storage unit 203 illustrated in FIG. 2. The external processing table illustrated in FIG. 8 is a table that assigns an external processing ID with respect to each external processing system and also associates an external processing system as a processing request destination, a processing content of the external processing system as the processing request destination, and the position in the display order of an externally processed image. The display order of the externally processed images illustrated in FIG. 8 is set by the display order setting unit 204. In the present exemplary embodiment, the display order of the externally processed images illustrated in FIG. 8 indicates the display order of thumbnails of a plurality of externally processed images generated by the external processing apparatuses 800 with respect to each of the series of the "chest front A" button 651 and the "chest front B" button 652 illustrated in FIG. 6. Thus, FIG. 8 illustrates, for example, the display order of thumbnails of externally processed images in the same series. For example, in FIG. 8, an externally processed image corresponding to the external processing ID "3" is an image obtained by the external processing apparatus 800-B (the external processing system B) performing processing 1, and the position in the display order of a thumbnail of the externally processed image is "3". That is, the thumbnail of the externally processed image corresponding to the external processing ID "3" is displayed after thumbnails of externally processed images corresponding to the external processing IDs "4" and "1" and displayed before a thumbnail of an externally processed image corresponding to the external processing ID "2".

A case is considered where, for example, the display order in the external processing table illustrated in FIG. 8 indicates the display order of thumbnails of externally processed images in the series of the "chest front A" button 651 illustrated in FIG. 6. In this case, only the thumbnail 650a of a single externally processed image is illustrated in the "chest front A" button 651 illustrated in FIG. 6. However, in a case where the display order in the external processing table illustrated in FIG. 8 is applied, thumbnails 650a of four externally processed images can be displayed. Among the thumbnails 650a of the four externally processed images that can be displayed in the "chest front A" button 651 illustrated in FIG. 6, for example, a thumbnail of an externally processed image corresponding to "1" indicated by the display order illustrated in FIG. 8 is then displayed at the leftmost position (the top). Next, for example, thumbnails of externally processed images corresponding to "2" and "3" indicated by the display order illustrated in FIG. 8 are displayed to the right of the thumbnail of the externally processed image corresponding to "1" indicated by the display order. Lastly, a thumbnail of an externally processed image corresponding to "4" indicated by the display order illustrated in FIG. 8 is displayed at the rightmost position (the end).

Alternatively, the display order illustrated in FIG. 8 can be set in ascending order according to the order of connection to the external processing apparatuses 800 by the radiation imaging apparatus 100. Yet alternatively, the display order illustrated in FIG. 8 can be statistically set according to the use or connection frequency of each external processing apparatus 800 that is stored in the storage unit 203, for example. Yet alternatively, the display order illustrated in FIG. 8 can be optionally set by the user through the operation unit 140. Yet alternatively, the display order illustrated in FIG. 8 can be set according to the processing content of each external processing apparatus 800 illustrated in FIG. 8. For example, a thumbnail of an externally processed image generated by an external processing apparatus 800 that executes a body motion detection process by fluoroscopic imaging to assist imaging is displayed to the left (before) of a thumbnail of an externally processed image generated by an external processing apparatus 800 that executes a foreign object detection process performed after imaging.

Figure 9:
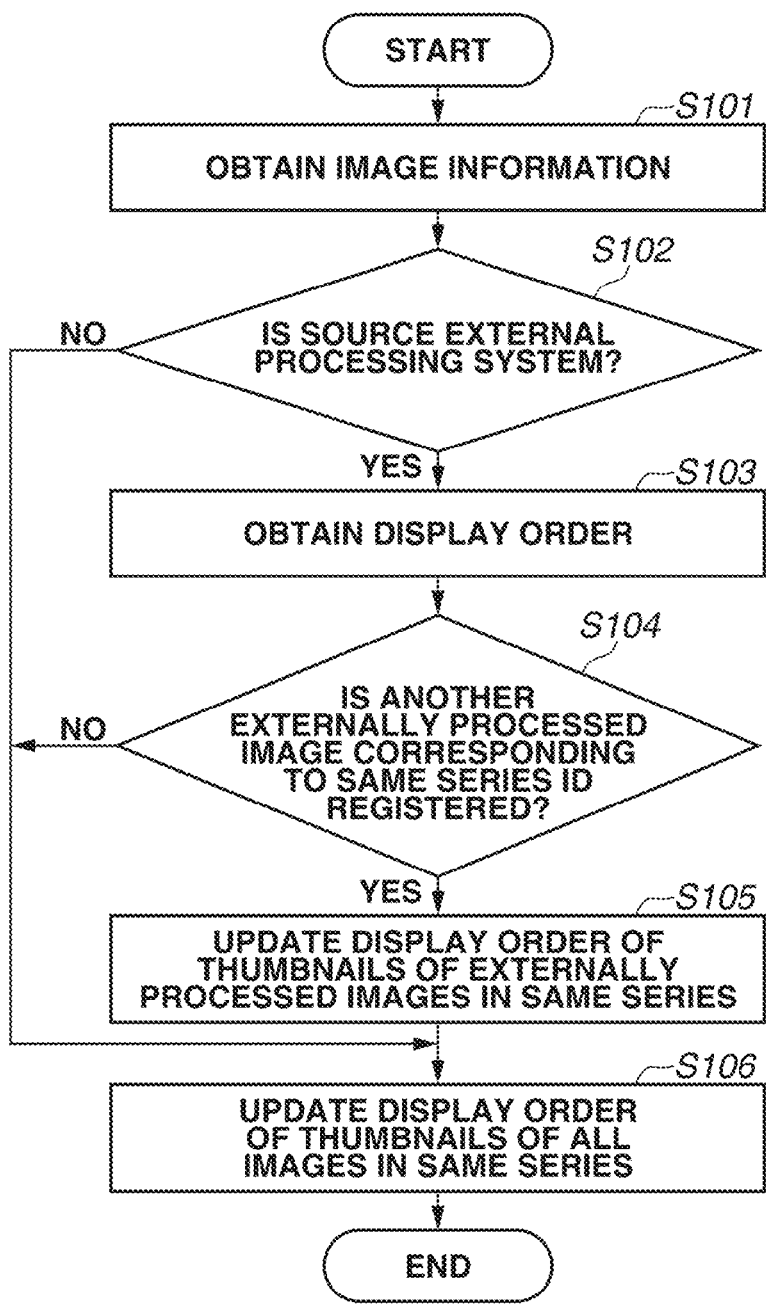
FIG. 9 is a flowchart illustrating an example of a processing procedure in a control method for controlling the radiation imaging apparatus according to the first exemplary embodiment of the present disclosure.

FIG. 9 is a flowchart illustrating an example of a processing procedure in a control method for controlling the radiation imaging apparatus 100 according to the first exemplary embodiment of the present disclosure. Specifically, FIG. 9 is a flowchart illustrating an example of a processing procedure when the overall control unit 120 sets the display order of thumbnails of a plurality of externally processed images obtained by the external processing apparatuses 800 processing a radiation image.

In step S101, for example, the display order setting unit 204 obtains image information regarding an image as a target, from the image table illustrated in FIG. 7 that is stored in the storage unit 203.

In step S102, for example, the display order setting unit 204 refers to the "source" illustrated in FIG. 7 in the image information obtained in step S101 and determines whether the source is an external processing apparatus 800 (an external processing system).

If, as a result of the determination in step S102, the source is an external processing apparatus 800 (an external processing system) (YES in step S102), the processing proceeds to step S103.

In step S103, the display order setting unit 204 refers to the "source" and the "processing content" illustrated in FIG. 7 in the image information obtained in step S101 and obtains the display order that matches the source and the processing content that are referred to from the external processing table illustrated in FIG. 8 and sets the obtained display order.

In step S104, for example, the display order setting unit 204 refers to the "series ID" illustrated in FIG. 7 in the image information obtained in step S101 and determines whether another externally processed image corresponding to the same series ID is registered.

If, as a result of the determination in step S104, another externally processed image corresponding to the same series ID is registered (YES in step S104), the processing proceeds to step S105.

In step S105, the display order setting unit 204 updates and sets the display order of thumbnails of a plurality of externally processed images with respect to each of the series of the "chest front A" button 651 and the "chest front B" button 652 illustrated in FIG. 6. For example, if, in the image table illustrated in FIG. 7, an externally processed image corresponding to the image ID "3" is a target, the position in the display order of a thumbnail of the externally processed image is "1" in a series corresponding to the series ID "1" based on the external processing table illustrated in FIG. 8. In the image table illustrated in FIG. 7, the position in the display order of a thumbnail of an externally processed image already present and corresponding to the image ID "2" is "4" in the series corresponding to the series ID "1" based on the external processing table illustrated in FIG. 8. The description will now be given on the assumption that the series corresponding to the series ID "1" is the "chest front A" button 651 illustrated in FIG. 6. In this case, the display control unit 150 performs, according to the display order updated and set by the display order setting unit 204, display control to display the thumbnail of the externally processed image corresponding to the image ID "3" and the thumbnail of the externally processed image corresponding to the image ID "2" in this order from the left (front) in the "chest front A" button 651 in FIG. 6.

If the process of step S105 is completed, the processing proceeds to step S106. If it is determined in step S102 that the source is not an external processing apparatus 800 (NO in step S102), or also if it is determined in step S104 that another externally processed image corresponding to the same series ID is not registered (NO in step S104), the processing proceeds to step S106.

In step S106, the display order setting unit 204 updates and sets the display order of all thumbnails including a thumbnail of the radiation image and the thumbnails of the externally processed images with respect to each of the series of the "chest front A" button 651 and the "chest front B" button 652 illustrated in FIG. 6. In this case, the display control unit 150 performs, according to the display order updated and set by the display order setting unit 204, control to display all the thumbnails in order with respect to each of the series of the "chest front A" button 651 and the "chest front B" button 652 illustrated in FIG. 6. In the present exemplary embodiment, an embodiment in which the display order of the thumbnail of the radiation image and the thumbnails of the externally processed images is set according to the specifications of the overall control unit 120 can be employed. Alternatively, an embodiment in which the display order of the thumbnail of the radiation image and the thumbnails of the externally processed images is optionally set by the user through the operation unit 140 can be employed.

When the process of step S106 is completed, the processing of the flowchart illustrated in FIG. 9 ends.

In the processing of the flowchart illustrated in FIG. 9, if the processing is suspended in the middle due to power failure of the radiation imaging apparatus 100, an embodiment can be employed in which the processing is started again from step S101 after the resumption of the processing. Alternatively, an embodiment can also be employed in which the storage unit 203 holds the progress of the suspended processing, the progress of the suspended processing is read from the storage unit 203 after the resumption of the processing, and the processing is resumed.

In the above-described radiation imaging apparatus 100 according to the first exemplary embodiment, the radiation detection unit 110 detects the radiation 301 incident on the radiation detection unit 110 and generates a radiation image. The input/output unit 207 (an obtaining unit) transmits the radiation image generated by the radiation detection unit 110 to an external processing apparatus 800 as a processing request destination, and obtains an externally processed image obtained by the external processing apparatus 800 as the processing request destination processing the radiation image from the external processing apparatus 800 as the processing request destination. The display order setting unit 204 sets the display order of a plurality of externally processed images (thumbnails) obtained by the input/output unit 207. The display control unit 150 then performs control to display the plurality of externally processed images (the thumbnails) on the display unit 160 according to the display order set by the display order setting unit 204.

According to this configuration, a plurality of externally processed images (thumbnails) is arranged in order and displayed according to the display order set in advance. Thus, the user can efficiently perform the work of confirming an externally processed image. This can prevent a decrease in the operability for the user and the incorrect recognition of an image.

In the radiation imaging apparatus 100 according to the first exemplary embodiment, the input/output unit 207 can obtain a plurality of externally processed images from the plurality of external processing apparatuses 800-A to 800-C. The display order setting unit 204 then sets the display order of the plurality of externally processed images (thumbnails) according to the types of the plurality of external processing apparatuses 800-A to 800-C(see FIG. 8). The display order setting unit 204 also sets the display order of the plurality of externally processed images (thumbnails) according to the type of the processing content of each external processing apparatus 800 (see FIG. 8). More specifically, in the radiation imaging apparatus 100 according to the first exemplary embodiment, the storage unit 203 stores information indicating the display order (see FIG. 8) determined according to the types of the plurality of external processing apparatuses 800-A to 800-C and the type of the processing content of each external processing apparatus 800. In this case, the display order setting unit 204 sets the display order of the plurality of externally processed images (thumbnails) based on the information indicating the display order stored in the storage unit 203.

A second exemplary embodiment of the present disclosure will now be described. In the following description of the second exemplary embodiment, items common to the first and second exemplary embodiments are not described, and items different from the first exemplary embodiment are described.

In the first exemplary embodiment, the display order is set based on which external processing apparatus 800 processes an externally processed image. In the second exemplary embodiment, an embodiment is employed in which the display order is set based on information regarding an imaging protocol. For example, if an imaging target part in an imaging protocol is a chest, an externally processed image (a thumbnail) obtained by an external processing apparatus 800 that performs processing, such as foreign object detection in a pneumothorax, can always be displayed at the beginning.

The schematic configuration of the radiation imaging system according to the second exemplary embodiment is similar to the schematic configuration of the radiation imaging system 10 according to the first exemplary embodiment illustrated in FIG. 1. The schematic configuration of the overall control unit 120 according to the second exemplary embodiment is similar to the schematic configuration of the overall control unit 120 according to the first exemplary embodiment illustrated in FIG. 2.

In the second exemplary embodiment, the overall control unit 120 identifies, when an externally processed image is obtained, an imaging method ID and an imaging protocol based on the image ID illustrated in FIG. 7 attached to the radiation image when the radiation image is transmitted to the external processing apparatus 800.

FIG. 10 is a diagram illustrating the second exemplary embodiment of the present disclosure and illustrating an example of the imaging method table stored in the storage unit 203 illustrated in FIG. 2. The imaging method table illustrated in FIG. 10 is a table that stores, with respect to each imaging method, settings such as an imaging method ID, the name of the imaging, a sensor as the type of the radiation detection unit 110 used in the imaging, and a prioritized external processing request destination (priority external processing). In the present exemplary embodiment, the display order setting unit 204 sets the position in the display order of an externally processed image (a thumbnail) obtained by an external processing apparatus 800 as a prioritized external processing request destination indicated by the priority external processing in FIG. 10 to "1". The display control unit 150 displays this image at the leftmost position (the top, i.e., the beginning). In the present exemplary embodiment, the position in the display order set by the display order setting unit 204 can be stored in the storage unit 203 and used as information for preferentially transmitting a radiation image to the external processing apparatus 800.

Figure 11:
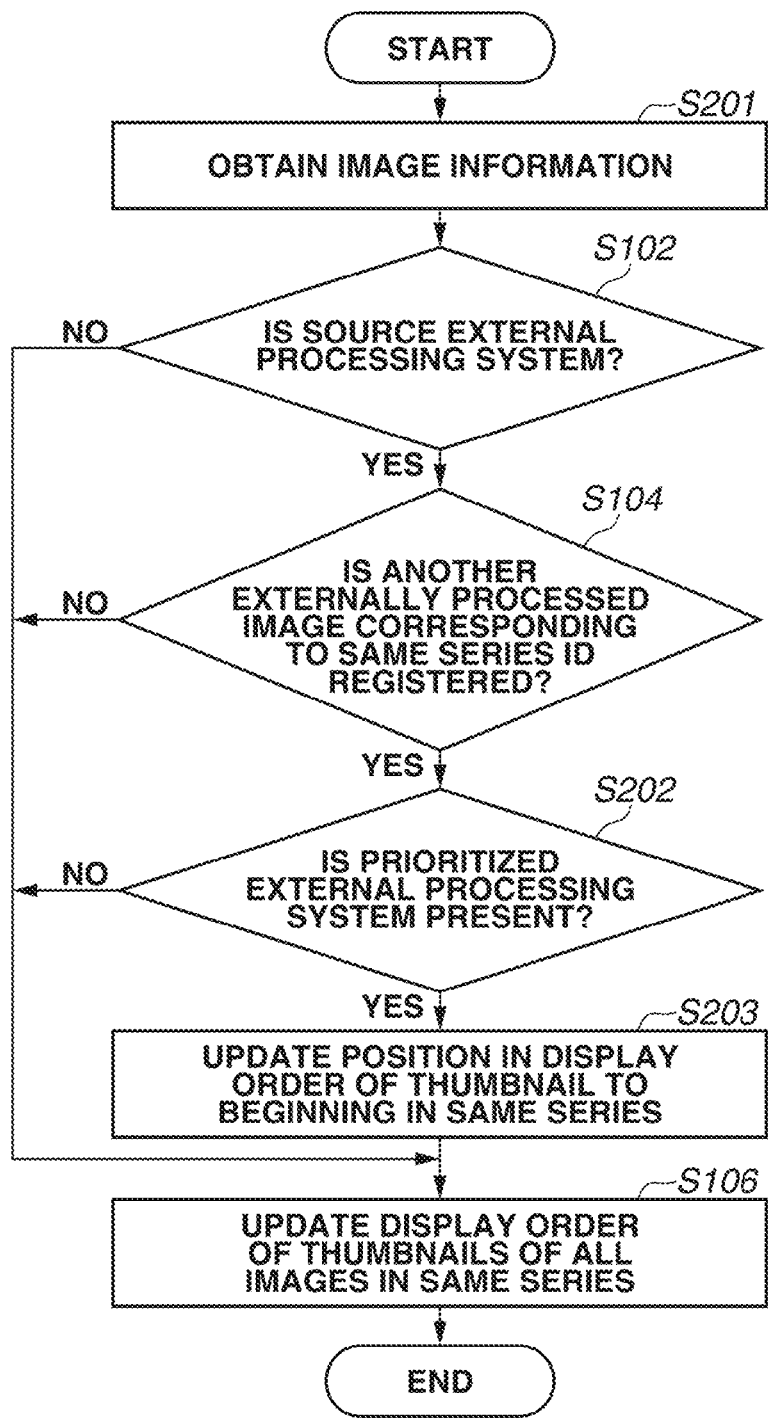
FIG. 11 is a flowchart illustrating an example of a processing procedure in a control method for controlling a radiation imaging apparatus according to the second exemplary embodiment of the present disclosure.

FIG. 11 is a flowchart illustrating an example of a processing procedure in a control method for controlling the radiation imaging apparatus 100 according to the second exemplary embodiment of the present disclosure. Specifically, FIG. 11 is a flowchart illustrating an example of a processing procedure when the overall control unit 120 sets the display order of thumbnails of a plurality of externally processed images obtained by the external processing apparatuses 800 processing a radiation image. In the flowchart illustrated in FIG. 11, processing steps similar to the processing steps in the flowchart illustrated in FIG. 9 are designated by the same step numbers, and are not described in detail.

In step S201, for example, the display order setting unit 204 obtains image information regarding an image as a target from the image table illustrated in FIG. 7 that is described in the storage unit 203.

In step S102, for example, the display order setting unit 204 refers to the "source" illustrated in FIG. 7 in the image information obtained in step S201 and determines whether the source is an external processing apparatus 800 (an external processing system).

If, as a result of the determination in step S102, the source is an external processing apparatus 800 (an external processing system) (YES in step S102), the processing proceeds to step S104.

In step S104, for example, the display order setting unit 204 refers to the "series ID" illustrated in FIG. 7 in the image information obtained in step S201 and determines whether another externally processed image corresponding to the same series ID is registered.

If, as a result of the determination in step S104, another externally processed image corresponding to the same series ID is registered (YES in step S104), the processing proceeds to step S202.

In step S202, for example, the display order setting unit 204 refers to the "priority external processing" in the imaging method table illustrated in FIG. 10 based on the imaging method ID illustrated in FIG. 7, and determines whether a prioritized external processing apparatus 800 (external processing system) is present.

If, as a result of the determination in step S202, a prioritized external processing apparatus 800 (external processing system) is present (YES in step S202), the processing proceeds to step S203.

In step S203, the display order setting unit 204 updates and sets the display order of thumbnails of a plurality of externally processed images with respect to each of the series of the "chest front A" button 651 and the "chest front B" button 652 illustrated in FIG. 6. Specifically, the display order setting unit 204 sets the position in the display order of a thumbnail of an externally processed image obtained by the prioritized external processing apparatus 800 (external processing system) indicated by the priority external processing in FIG. 10 to "1". The display control unit 150 then displays, according to the setting of this display order, the thumbnail of the externally processed image obtained by the prioritized external processing apparatus 800 (external processing system) at the leftmost position (the top, i.e., the beginning) among the thumbnails of the plurality of externally processed images in this series.

If the process of step S203 is completed, or if it is determined in step S202 that a prioritized external processing apparatus 800 (external processing system) is not present (NO in step S202), the processing proceeds to step S106. If it is also determined in step S102 that the source is not an external processing apparatus 800 (NO in step S102), or also if it is determined in step S104 that another externally processed image corresponding to the same series ID is not registered (NO in step S104), the processing proceeds to step S106.

In step S106, the display order setting unit 204 updates and sets the display order of all thumbnails including a thumbnail of the radiation image and the thumbnails of the externally processed images with respect to each of the series of the "chest front A" button 651 and the "chest front B" button 652 illustrated in FIG. 6. In this case, according to the display order updated and set by the display order setting unit 204, the display control unit 150 performs control to display all the thumbnails in order with respect to each of the series of the "chest front A" button 651 and the "chest front B" button 652 illustrated in FIG. 6. In the present exemplary embodiment, an embodiment can be employed in which the display order of the thumbnail of the radiation image and the thumbnails of the externally processed images is set according to the specifications of the overall control unit 120. Alternatively, an embodiment can be employed in which the display order of the thumbnail of the radiation image and the thumbnails of the externally processed images is optionally set by the user through the operation unit 140.

When the process of step S106 is completed, the processing of the flowchart illustrated in FIG. 11 ends.

In the radiation imaging apparatus 100 according to the second exemplary embodiment, the input/output unit 207 can obtain a plurality of externally processed images from the plurality of external processing apparatuses 800-A to 800-C. The display order setting unit 204 then sets the position in the display order of an externally processed image (a thumbnail) obtained by a prioritized external processing apparatus 800 before the position in the display order of an externally processed image (a thumbnail) obtained by another external processing apparatus 800 except for the prioritized external processing apparatus 800.

According to this configuration, an externally processed image (a thumbnail) obtained by a prioritized external processing apparatus 800 is displayed before an externally processed image (a thumbnail) obtained by another external processing apparatus 800. Thus, the user can efficiently perform the work of confirming an externally processed image. This can prevent a decrease in the operability for the user and the incorrect recognition of an image.

An embodiment obtained by combining the present exemplary embodiment and the first exemplary embodiment is also included in the present disclosure.

A third exemplary embodiment of the present disclosure will now be described. In the following description of the third exemplary embodiment, items common to the first and second exemplary embodiments and the third exemplary embodiment are not described, and items different from the first and second exemplary embodiments are described.

In the first exemplary embodiment, the display order is set based on which external processing apparatus 800 processes an externally processed image. In the third exemplary embodiment, an embodiment is employed in which the display order is set based on the presence or absence of the output of the radiation image as the original image of an externally processed image.

The schematic configuration of the radiation imaging system according to the third exemplary embodiment is similar to the schematic configuration of the radiation imaging system 10 according to the first exemplary embodiment illustrated in FIG. 1. The schematic configuration of the overall control unit 120 according to the third exemplary embodiment is similar to the schematic configuration of the overall control unit 120 according to the first exemplary embodiment illustrated in FIG. 2.

Figure 12:
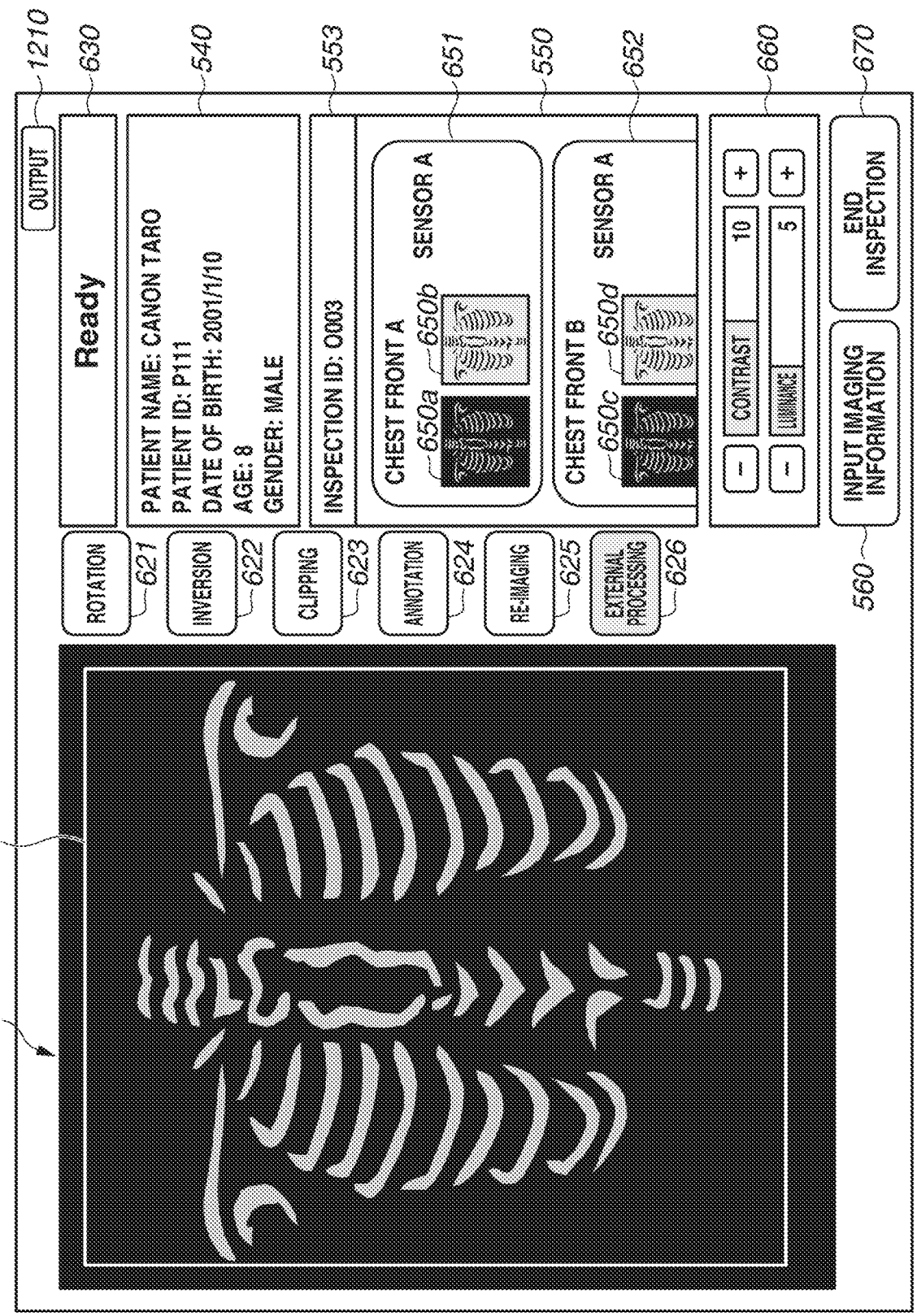
FIG. 12 is a diagram illustrating a third exemplary embodiment of the present disclosure and illustrating an example of the imaging screen displayed on the display unit illustrated in FIG. 1.

FIG. 12 is a diagram illustrating the third exemplary embodiment of the present disclosure and illustrating an example of an imaging screen displayed on the display unit 160 illustrated in FIG. 1. In FIG. 12, components similar to the components illustrated in FIG. 6 are designated by the same signs, and are not described in detail.

The imaging screen illustrated in FIG. 12 has a configuration in which an "output" button 1210 is added to the imaging screen illustrated in FIG. 6. If the "output" button 1210 is pressed, for example, a radiation image displayed in the image display area 610 is output to a specified output destination (e.g., one or more of the PACS 600, the printer 700, and the ROM of the radiation imaging apparatus 100) different from the external processing apparatuses 800. In a case where the user presses the "output" button 1210, a thumbnail of an externally processed image of which the original image is a radiation image before being output is used as a basis for the determination of the output of the radiation image. Thus, an embodiment can be employed in which the position in the display order of the thumbnail of the externally processed image is set to "1", and the thumbnail of the externally processed image is displayed at the beginning. An embodiment can be employed in which a thumbnail of an externally processed image of which the original image is a radiation image that is already output to a specified output destination is displayed behind.

In addition to an operation on the "output" button 1210, the case of automatic output set by an imaging protocol is also similarly applicable to the present exemplary embodiment.

FIG. 13 is a diagram illustrating the third exemplary embodiment of the present disclosure and illustrating an example of an image table that stores image information regarding a radiation image obtained by the radiation imaging apparatus 100 illustrated in FIG. 1 and an externally processed image obtained by each external processing apparatus 800 illustrated in FIG. 1. The image table illustrated in FIG. 13 is stored in the storage unit 203. The image table illustrated in FIG. 13 is a table that stores, with respect to each image, an image ID, a series ID, an imaging method ID, a source having obtained the image, a processing content of an external processing system indicated by the source, and information indicating whether the radiation image obtained by the radiation imaging apparatus 100 is already output. In the image table illustrated in FIG. 13, if "output" indicates "completed", this indicates that the radiation image is already output to a specified output destination. If the "output" is a blank, this indicates that the radiation image is not output. In FIG. 13, the same components as the components illustrated in FIG. 7 are written in the same manner, and are not described in detail.

In the third exemplary embodiment, when an externally processed image is obtained, the overall control unit 120 identifies an imaging method ID and an imaging protocol based on the image ID illustrated in FIG. 13 attached to the radiation image when the radiation image is transmitted to the external processing apparatus 800.

Figure 14:
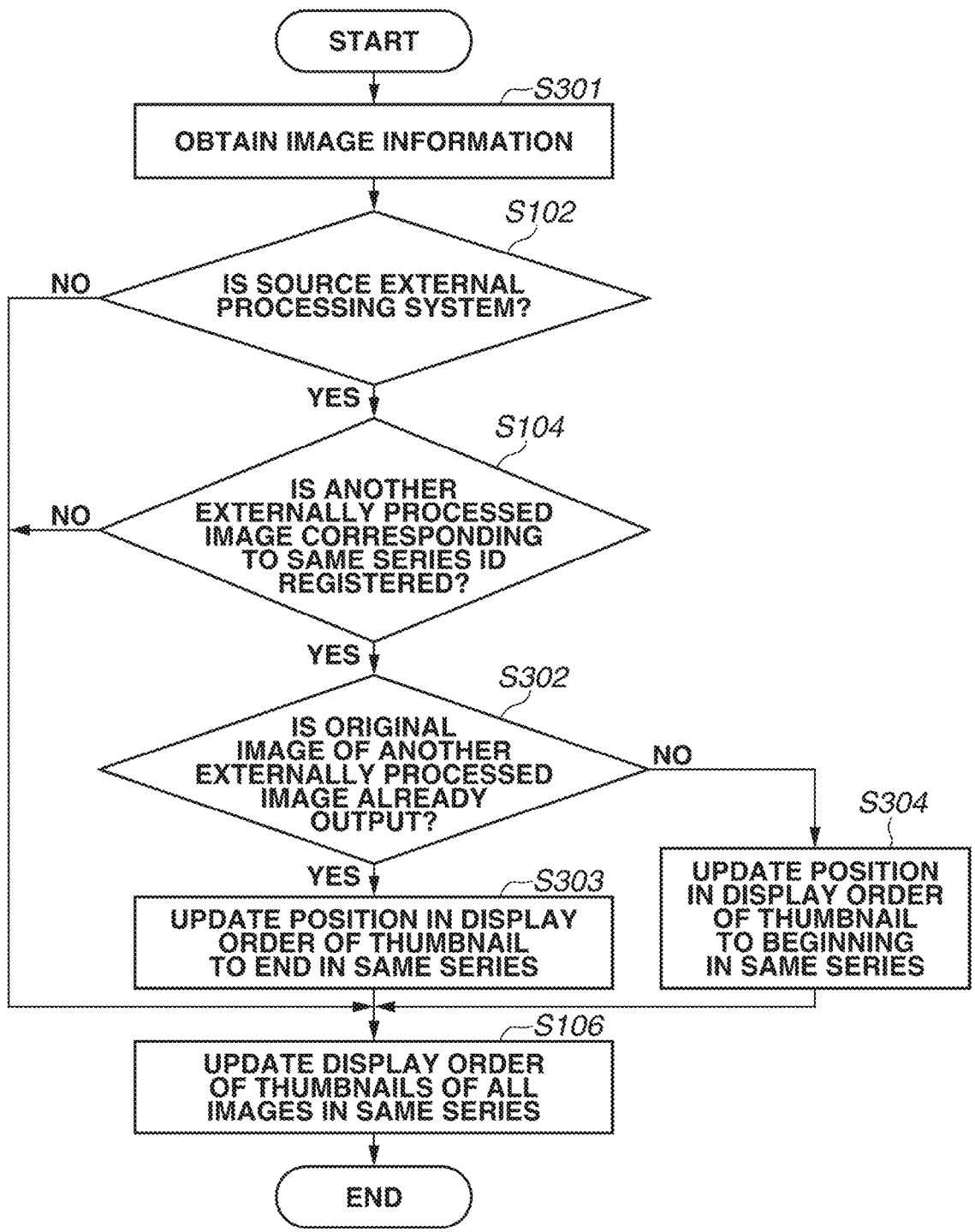
FIG. 14 is a flowchart illustrating an example of a processing procedure in a control method for controlling a radiation imaging apparatus according to the third exemplary embodiment of the present disclosure.

FIG. 14 is a flowchart illustrating an example of a processing procedure in a control method for controlling the radiation imaging apparatus 100 according to the third exemplary embodiment of the present disclosure. Specifically, FIG. 14 is a flowchart illustrating an example of a processing procedure when the overall control unit 120 sets the display order of thumbnails of a plurality of externally processed images obtained by the external processing apparatuses 800 processing radiation images. In the flowchart illustrated in FIG. 14, processing steps similar to the processing steps in the flowchart illustrated in FIG. 9 are designated by the same step numbers, and are not described in detail.

In step S301, for example, the display order setting unit 204 obtains image information regarding an image as a target from the image table illustrated in FIG. 13 that is stored in the storage unit 203.

In step S102, for example, the display order setting unit 204 refers to the "source" illustrated in FIG. 13 in the image information obtained in step S301, and determines whether the source is an external processing apparatus 800 (an external processing system).

If, as a result of the determination in step S102, the source is an external processing apparatus 800 (an external processing system) (YES in step S102), the processing proceeds to step S104.

In step S104, for example, the display order setting unit 204 refers to the "series ID" illustrated in FIG. 13 in the image information obtained in step S301 and determines whether another externally processed image corresponding to the same series ID is registered.

If, as a result of the determination in step S104, another externally processed image corresponding to the same series ID is registered (YES in step S104), the processing proceeds to step S302.

In step S302, for example, the display order setting unit 204 refers to the "output" illustrated in FIG. 13 and determines whether the radiation image as the original image of another externally processed image registered according to the determination in step S104 is already output.

If, as a result of the determination in step S302, the radiation image as the original image of another externally processed image registered according to the determination in step S104 is already output (YES in step S302), the processing proceeds to step S303.

In step S303, the display order setting unit 204 sets the position in the display order of a thumbnail of the externally processed image of which the original image is the radiation image that is already output after the position in the display order of a thumbnail of an externally processed image of which the original image is a radiation image that is not already output. The display control unit 150 then displays, according to the setting of this display order, the thumbnail of the externally processed image of which the original image is the radiation image that is already output to the right of (after) the thumbnail of the externally processed image of which the original image is the radiation image that is not already output in this series. If there is one single radiation image that is already output in this series, the display control unit 150 displays a thumbnail of an externally processed image of which the original image is the radiation image that is already output at the rightmost position (the end) among thumbnails of a plurality of externally processed images in this series.

If, in contrast, the radiation image as the original image of another externally processed image registered according to the determination in step S104 is not already output as a result of the determination in step S302 (NO in step S302), the processing proceeds to step S304.

In step S304, the display order setting unit 204 sets the position in the display order of a thumbnail of the externally processed image of which the original image is the radiation image that is not already output before the position in the display order of a thumbnail of an externally processed image of which the original image is a radiation image that is already output. The display control unit 150 then displays, according to the setting of this display order, the thumbnail of the externally processed image of which the original image is the radiation image that is not already output to the left (before) of the thumbnail of the externally processed image of which the original image is the radiation image that is already output in this series. If there is one single radiation image that is not already output in this series, the display control unit 150 displays a thumbnail of an externally processed image of which the original image is the radiation image that is not already output at the leftmost position (the beginning) among thumbnails of a plurality of externally processed images in this series.

Alternatively, the radiation imaging apparatus 100 can store the display order set in step S303 or S304 in the storage unit 203 and use the display order as the output order when the inspection ends, or can use the display order as the output order for automatic output.

When the process of step S303 is completed, or when the process of step S304 is completed, the processing proceeds to step S106. Further, if it is determined in step S102 that the source is not an external processing apparatus 800 (NO in step S102), or if it is determined in step S104 that another externally processed image corresponding to the same series ID is not registered (NO in step S104), the processing proceeds to step S106.

In step S106, the display order setting unit 204 updates and sets the display order of all thumbnails including thumbnails of the radiation images and the thumbnails of the externally processed images with respect to each of the series of the "chest front A" button 651 and the "chest front B" button 652 illustrated in FIG. 6. In this case, according to the display order updated and set by the display order setting unit 204, the display control unit 150 performs control to display all the thumbnails in order with respect to each of the series of the "chest front A" button 651 and the "chest front B" button 652 illustrated in FIG. 6. In the present exemplary embodiment, an embodiment can be employed in which the display order of the thumbnails of the radiation images and the thumbnails of the externally processed images is set according to the specifications of the overall control unit 120. Alternatively, an embodiment can be employed in which the display order of the thumbnails of the radiation images and the thumbnails of the externally processed images is optionally set by the user through the operation unit 140.

When the process of step S106 is completed, the processing of the flowchart illustrated in FIG. 14 ends.

In the radiation imaging apparatus 100 according to the third exemplary embodiment described above, the display order setting unit 204 sets the display order of a plurality of externally processed images (thumbnails) according to whether the radiation images are already output to output destinations different from the external processing apparatuses 800.

According to this configuration, a plurality of externally processed images (thumbnails) is displayed in the display order set according to whether the radiation images are already output. Thus, the user can efficiently perform the work of confirming an externally processed image. This can prevent a decrease in the operability for the user and the incorrect recognition of an image.

An embodiment obtained by combining the present exemplary embodiment and at least one of the first and second exemplary embodiments is also included in the present disclosure.

Next, a fourth exemplary embodiment of the present disclosure is described. In the following description of the fourth exemplary embodiment, items common to the first to third exemplary embodiments are not described, and items different from the first to third exemplary embodiments are described.

In the above-described first exemplary embodiment, the display order is set based on which external processing apparatus 800 processes an externally processed image. In the fourth exemplary embodiment, an embodiment is employed in which the display order is set based on whether the radiation image as the original image of an externally processed image is already rejected or deleted.

The schematic configuration of the radiation imaging system according to the fourth exemplary embodiment is similar to the schematic configuration of the radiation imaging system 10 according to the first exemplary embodiment illustrated in FIG. 1. The schematic configuration of the overall control unit 120 according to the fourth exemplary embodiment is similar to the schematic configuration of the overall control unit 120 according to the first exemplary embodiment illustrated in FIG. 2.

FIG. 15 is a diagram illustrating the fourth exemplary embodiment of the present disclosure and illustrating an example of an image table that stores image information regarding a radiation image obtained by the radiation imaging apparatus 100 illustrated in FIG. 1 and an externally processed image obtained by each external processing apparatus 800 illustrated in FIG. 1. The image table illustrated in FIG. 15 is stored in the storage unit 203. The image table illustrated in FIG. 15 is a table that stores, with respect to each image, an image ID, a series ID, an imaging method ID, a source, a processing content of an external processing system, and information indicating whether a radiation image (which may include an externally processed image) is already rejected or deleted. An embodiment may be employed in which if a radiation image (which may include an externally processed image) is already rejected or deleted, image information regarding an image as a target is deleted from the image table illustrated in FIG. 15.

Figure 16:
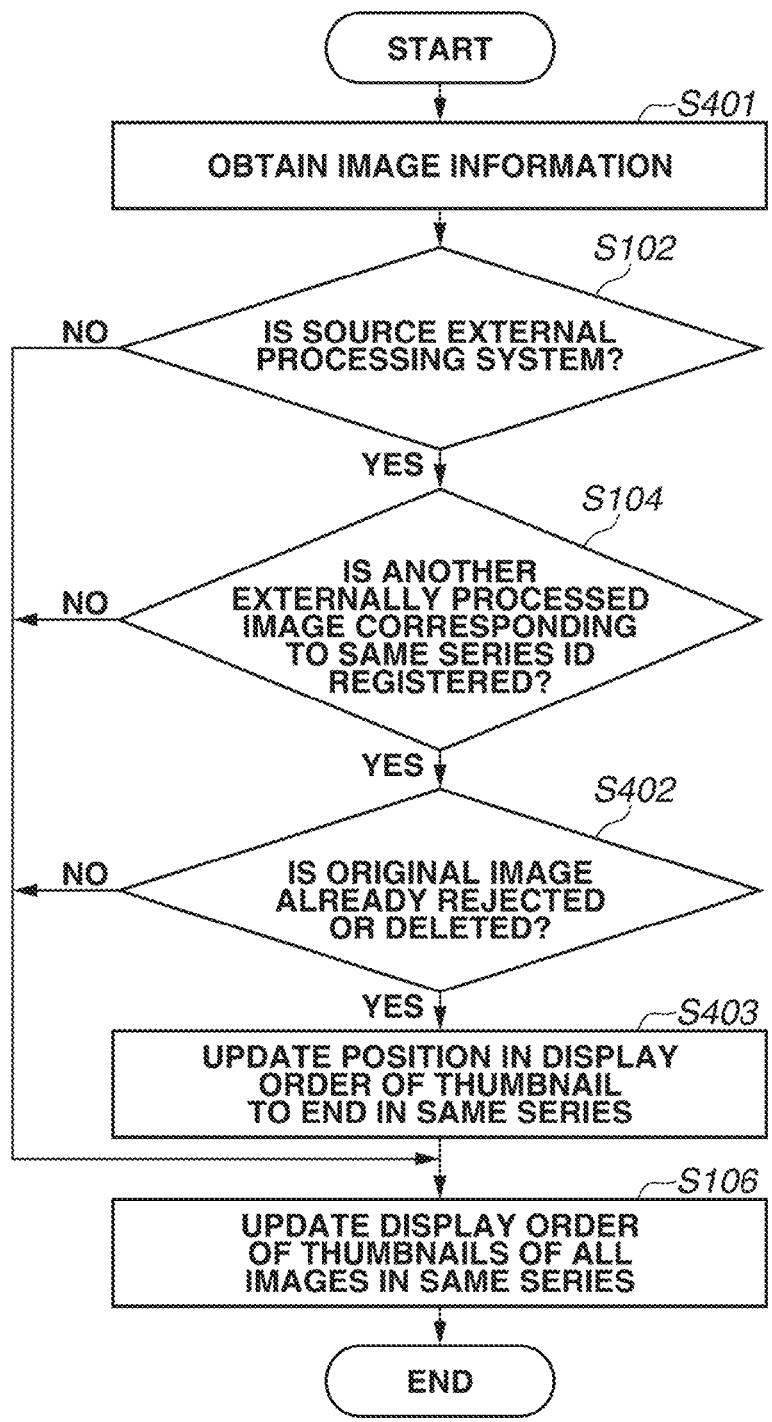
FIG. 16 is a flowchart illustrating an example of a processing procedure in a control method for controlling a radiation imaging apparatus according to the fourth exemplary embodiment of the present disclosure.

FIG. 16 is a flowchart illustrating an example of a processing procedure in a control method for controlling the radiation imaging apparatus 100 according to the fourth exemplary embodiment of the present disclosure. Specifically, FIG. 16 is a flowchart illustrating an example of a processing procedure when the overall control unit 120 sets the display order of thumbnails of a plurality of externally processed images obtained by the external processing apparatuses 800 processing radiation images. In the flowchart illustrated in FIG. 16, processing steps similar to the processing steps in the flowchart illustrated in FIG. 9 are designated by the same step numbers, and are not described in detail.

In step S401, for example, the display order setting unit 204 obtains image information regarding an image as a target from the image table illustrated in FIG. 15 that is described in the storage unit 203.

In step S102, for example, the display order setting unit 204 refers to the "source" illustrated in FIG. 15 in the image information obtained in step S401 and determines whether the source is an external processing apparatus 800 (an external processing system).

If, as a result of the determination in step S102, the source is an external processing apparatus 800 (an external processing system) (YES in step S102), the processing proceeds to step S104.

In step S104, for example, the display order setting unit 204 refers to the "series ID" illustrated in FIG. 15 in the image information obtained in step S401 and determines whether another externally processed image corresponding to the same series ID is registered.

If, as a result of the determination in step S104, another externally processed image corresponding to the same series ID is registered (YES in step S104), the processing proceeds to step S402.

In step S402, for example, the display order setting unit 204 refers to "rejection (or deletion)" illustrated in FIG. 15 and determines whether the radiation image as the original image of another externally processed image registered according to the determination in step S104 is already rejected or deleted.

If, as a result of the determination in step S402, the radiation image as the original image of another externally processed image registered according to the determination in step S104 is already rejected or deleted (YES in step S402), the processing proceeds to step S403.

In step S403, the display order setting unit 204 sets the position in the display order of a thumbnail of the externally processed image of which the original image is the radiation image that is already rejected or deleted after the position in the display order of a thumbnail of an externally processed image of which the original image is a radiation image that is not already rejected or deleted. Then, according to the setting of this display order, the display control unit 150 displays the thumbnail of the externally processed image related to the radiation image that is already rejected or deleted, to the right of (after) the thumbnail of the externally processed image related to the radiation image that is not already rejected or deleted in this series. If only a single radiation image is already rejected or deleted in this series, the display control unit 150 displays a thumbnail of an externally processed image of which the original image is the radiation image that is already rejected or deleted, at the rightmost position (the end) among thumbnails of a plurality of externally processed images in this series.

When the process of step S403 is completed, or if it is determined in step S402 that the radiation image as the original image of the externally processed image is not already rejected or deleted (NO in step S402), the processing proceeds to step S106. If it is also determined in step S102 that the source is not an external processing apparatus 800 (NO in step S102), or also if it is determined in step S104 that another externally processed image corresponding to the same series ID is not registered (NO in step S104), the processing proceeds to step S106.

In step S106, the display order setting unit 204 updates and sets the display order of all thumbnails including thumbnails of the radiation images and the thumbnails of the externally processed images with respect to each of the series of the "chest front A" button 651 and the "chest front B" button 652 illustrated in FIG. 6. In this case, the display control unit 150 performs control to display all the thumbnails in order with respect to each of the series of the "chest front A" button 651 and the "chest front B" button 652 illustrated in FIG. 6, according to the display order updated and set by the display order setting unit 204. In the present exemplary embodiment, an embodiment can be employed in which the display order of the thumbnails of the radiation images and the thumbnails of the externally processed images is set according to the specifications of the overall control unit 120. Alternatively, an embodiment can be employed in which the display order of the thumbnails of the radiation images and the thumbnails of the externally processed images is optionally set by the user through the operation unit 140.

When the process of step S106 is completed, the processing of the flowchart illustrated in FIG. 16 ends.

In the radiation imaging apparatus 100 according to the fourth exemplary embodiment, the display order setting unit 204 sets the display order of a plurality of externally processed images (thumbnails) according to whether the radiation images are already rejected or deleted.

According to this configuration, a plurality of externally processed images (thumbnails) is displayed in the display order set according to whether the radiation images are already rejected or deleted. Thus, the user can efficiently perform the work of confirming an externally processed image. This can prevent a decrease in the operability for the user and the incorrect recognition of an image.

An embodiment obtained by combining the present exemplary embodiment and at least one of the first to third exemplary embodiments is also included in the present disclosure.

Next, a fifth exemplary embodiment of the present disclosure is described. In the following description of the fifth exemplary embodiment, items common to the first to fourth exemplary embodiments are not described, and items different from the first to fourth exemplary embodiments are described.

In the first exemplary embodiment, the display order is set based on which external processing apparatus 800 processes an externally processed image. In the fifth exemplary embodiment, an embodiment is employed in which the display order is set based on whether the radiation image as the original image of an externally processed image is already deleted.

The schematic configuration of the radiation imaging system according to the fifth exemplary embodiment is similar to the schematic configuration of the radiation imaging system 10 according to the first exemplary embodiment illustrated in FIG. 1. The schematic configuration of the overall control unit 120 according to the fifth exemplary embodiment is similar to the schematic configuration of the overall control unit 120 according to the first exemplary embodiment illustrated in FIG. 2.

Figure 17:
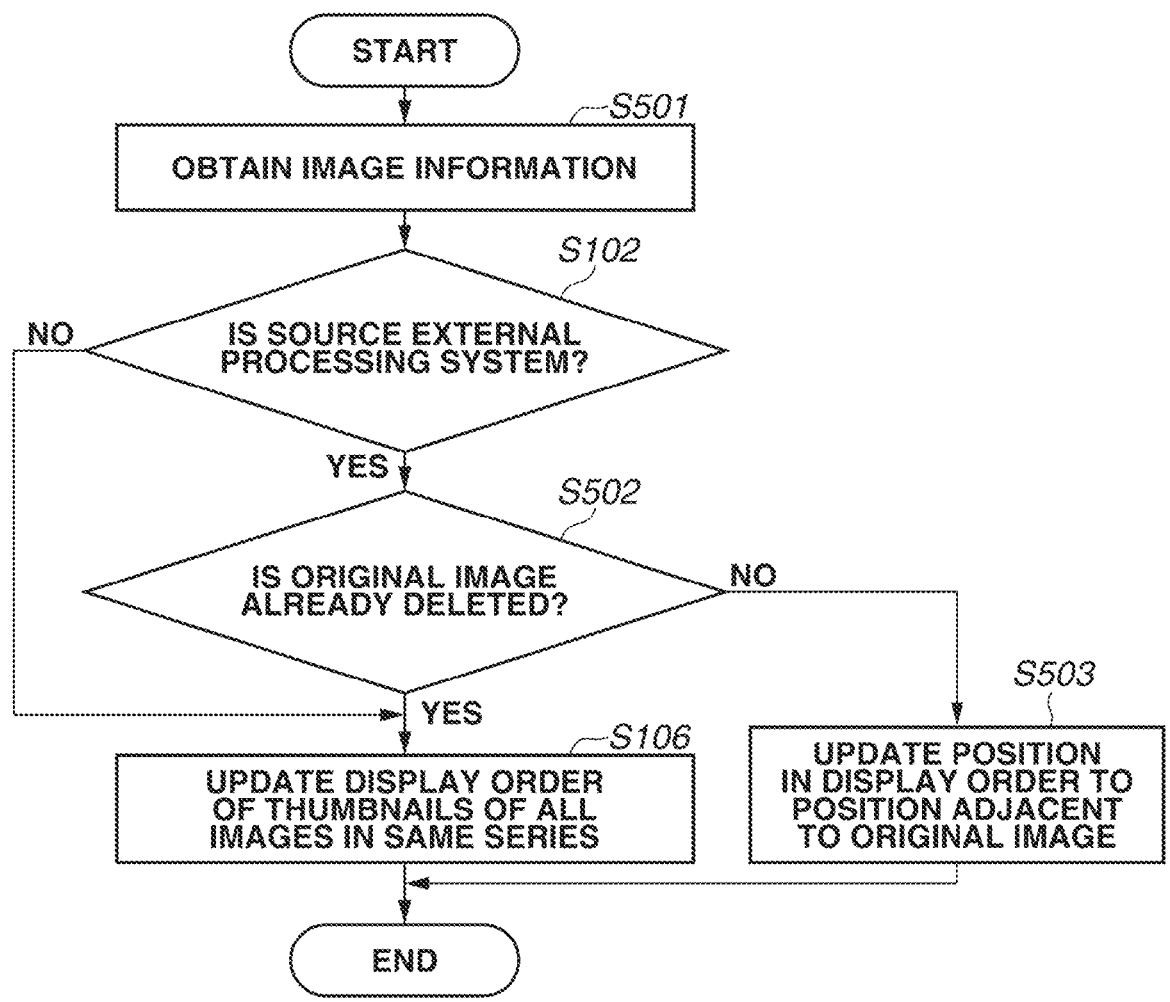
FIG. 17 is a flowchart illustrating an example of a processing procedure in a control method for controlling a radiation imaging apparatus according to a fifth exemplary embodiment of the present disclosure.

FIG. 17 is a flowchart illustrating an example of a processing procedure in a control method for controlling the radiation imaging apparatus 100 according to the fifth exemplary embodiment of the present disclosure. Specifically, FIG. 17 is a flowchart illustrating an example of a processing procedure when the overall control unit 120 sets the display order of thumbnails of a plurality of externally processed images obtained by the external processing apparatuses 800 processing radiation images. In the flowchart illustrated in FIG. 17, processing steps similar to the processing steps in the flowchart illustrated in FIG. 9 are designated by the same step numbers, and are not described in detail.

In step S501, for example, the display order setting unit 204 obtains image information regarding an image as a target from the image table illustrated in FIG. 15 that is described in the storage unit 203.

In step S102, for example, the display order setting unit 204 refers to the "source" illustrated in FIG. 15 in the image information obtained in step S501, and determines whether the source is an external processing apparatus 800 (an external processing system).

If, as a result of the determination in step S102, the source is an external processing apparatus 800 (an external processing system) (YES in step S102), the processing proceeds to step S502.

In step S502, for example, the display order setting unit 204 determines whether the radiation image as the original image of an externally processed image is already deleted. In the process of step S502, for example, the display order setting unit 204 can make the determination with reference to the "rejection (or deletion)" illustrated in FIG. 15.

If, as a result of the determination in step S502, the radiation image as the original image of the externally processed image is not already deleted (NO in step S502), the processing proceeds to step S503.

In step S503, the display order setting unit 204 sets, with respect to each radiation image that is not already deleted, the position in the display order of a thumbnail of the externally processed image of which the original image is the radiation image so that the thumbnail of the externally processed image is located adjacent to the radiation image. The display control unit 150 then displays, with respect to each radiation image that is not already deleted in this series, the thumbnail of the externally processed image of which the original image is the radiation image adjacent to the radiation image, according to the setting of this display order. At this time, the thumbnail of the externally processed image of which the original image is the radiation image can be adjacent to either the right or the left of the radiation image. An embodiment can also be employed in which the display position of the thumbnail of the externally processed image is uniquely set by the overall control unit 120. Alternatively, an embodiment can be employed in which the display position of the thumbnail of the externally processed image is optionally set by the user through the operation unit 140.

If, as a result of the determination in step S502, the radiation image as the original image of the externally processed image is already deleted (YES in step S502), or if it is determined in step S102 that the source is not an external processing apparatus 800 (NO in step S102), the processing proceeds to step S106.

In step S106, the display order setting unit 204 updates and sets the display order of all thumbnails including thumbnails of the radiation images and the thumbnails of the externally processed images with respect to each of the series of the "chest front A" button 651 and the "chest front B" button 652 illustrated in FIG. 6. In this case, the display control unit 150 performs control to display all the thumbnails in order with respect to each of the series of the "chest front A" button 651 and the "chest front B" button 652 illustrated in FIG. 6, according to the display order updated and set by the display order setting unit 204. In the present exemplary embodiment, an embodiment can be employed in which the display order of the thumbnails of the radiation images and the thumbnails of the externally processed images is set according to the specifications of the overall control unit 120. Alternatively, an embodiment can be employed in which the display order of the thumbnails of the radiation images and the thumbnails of the externally processed images is optionally set by the user through the operation unit 140.

If the process of step S503 is completed, or if the process of step S106 is completed, the processing of the flowchart illustrated in FIG. 17 ends.

In the above-described radiation imaging apparatus 100 according to the fifth exemplary embodiment, the display order setting unit 204 sets, with respect to each radiation image that is not already deleted, the position in the display order of a thumbnail of an externally processed image of which the original image is the radiation image so that the thumbnail of the externally processed image is located adjacent to the radiation image.

According to this configuration, an externally processed image (a thumbnail) is displayed continuous with the radiation image as the original image. Thus, the user can efficiently perform the work of confirming an externally processed image. This can prevent a decrease in the operability for the user and the incorrect recognition of an image.

An embodiment obtained by combining the present exemplary embodiment and at least one of the first to fourth exemplary embodiments is also included in the present disclosure.

Next, a sixth exemplary embodiment of the present disclosure is described. In the following description of the sixth exemplary embodiment, items common to the first to fifth exemplary embodiments are not described, and items different from the first to fifth exemplary embodiments are described.

In the first exemplary embodiment, the display order is set based on which external processing apparatus 800 processes an externally processed image. In the sixth exemplary embodiment, an embodiment is employed in which the display order is set based on the transmission order of the radiation images as the original images of externally processed images.

The schematic configuration of the radiation imaging system according to the sixth exemplary embodiment is similar to the schematic configuration of the radiation imaging system 10 according to the first exemplary embodiment illustrated in FIG. 1. The schematic configuration of the overall control unit 120 according to the sixth exemplary embodiment is similar to the schematic configuration of the overall control unit 120 according to the first exemplary embodiment illustrated in FIG. 2.

FIG. 18 is a diagram illustrating the sixth exemplary embodiment of the present disclosure and illustrating an example of an image table that stores image information regarding a radiation image obtained by the radiation imaging apparatus 100 illustrated in FIG. 1 and an externally processed image obtained by each external processing apparatus 800 illustrated in FIG. 1. The image table illustrated in FIG. 18 is stored in the storage unit 203. The image table illustrated in FIG. 18 is a table that stores, with respect to each image, an image ID, a series ID, an imaging method ID, a source, a processing content of an external processing system, and a transmission ID indicating the position in the transmission order of a radiation image to an external processing apparatus 800 (an external processing system). The transmission ID is assigned in ascending order and updated every time a radiation image is transmitted to an external processing apparatus 800 (an external processing system).

FIG. 19 is a flowchart illustrating an example of a processing procedure in a control method for controlling the radiation imaging apparatus 100 according to the sixth exemplary embodiment of the present disclosure. Specifically, FIG. 19 is a flowchart illustrating an example of a processing procedure when the overall control unit 120 sets the display order of thumbnails of a plurality of externally processed images obtained by the external processing apparatuses 800 processing radiation images. In the flowchart illustrated in FIG. 19, processing steps similar to the processing steps in the flowchart illustrated in FIG. 9 are designated by the same step numbers, and are not described in detail.

In step S601, for example, the display order setting unit 204 obtains image information regarding an image as a target from the image table illustrated in FIG. 18 that is described in the storage unit 203.

In step S102, for example, the display order setting unit 204 refers to the "source" illustrated in FIG. 18 in the image information obtained in step S601, and determines whether the source is an external processing apparatus 800 (an external processing system).

If, as a result of the determination in step S102, the source is an external processing apparatus 800 (an external processing system) (YES in step S102), the processing proceeds to step S104.

In step S104, for example, the display order setting unit 204 refers to the "series ID" illustrated in FIG. 18 in the image information obtained in step S601, and determines whether another externally processed image corresponding to the same series ID is registered.

If, as a result of the determination in step S104, another externally processed image corresponding to the same series ID is registered (YES in step S104), the processing proceeds to step S602.

In step S602, the display order setting unit 204 refers to "transmission ID" illustrated in FIG. 18, and according to the transmission order indicated by the transmission ID, sets the display order of thumbnails of a plurality of externally processed images in this series. Specifically, the display order setting unit 204 sets the position in the display order of an externally processed image of which the original image is a radiation image transmitted earlier, before the position in the display order of an externally processed image of which the original image is a radiation image transmitted later. According to the setting of this display order, the display control unit 150 then arranges and displays the thumbnails of the plurality of externally processed images in this series. For example, in the image table illustrated in FIG. 18, the transmission ID of an externally processed image corresponding to the image ID "3" is "1", and the transmission ID of an externally processed image already present and corresponding to the image ID "2" is "2". In this case, the display control unit 150 sets the display order of thumbnails of externally processed images in this series to display a thumbnail of the externally processed image corresponding to the image ID "3" and a thumbnail of the externally processed image corresponding to the image ID "2" in this order from the left.

When the process of step S602 is completed, the processing proceeds to step S106. If it is determined in step S102 that the source is not an external processing apparatus 800 (NO in step S102), or if it is determined in step S104 that another externally processed image corresponding to the same series ID is not registered (NO in step S104), the processing proceeds to step S106.

In step S106, the display order setting unit 204 updates and sets the display order of all thumbnails including thumbnails of the radiation images and the thumbnails of the externally processed images with respect to each of the series of the "chest front A" button 651 and the "chest front B" button 652 illustrated in FIG. 6. In this case, according to the display order updated and set by the display order setting unit 204, the display control unit 150 performs control to display all the thumbnails in order with respect to each of the series of the "chest front A" button 651 and the "chest front B" button 652 illustrated in FIG. 6. In the present exemplary embodiment, an embodiment can be employed in which the display order of the thumbnails of the radiation images and the thumbnails of the externally processed images is set according to the specifications of the overall control unit 120. Alternatively, an embodiment can be employed in which the display order of the thumbnails of the radiation images and the thumbnails of the externally processed images is optionally set by the user through the operation unit 140.

When the process of step S106 is completed, the processing of the flowchart illustrated in FIG. 19 ends.

In the radiation imaging apparatus 100 according to the sixth exemplary embodiment, the display order setting unit 204 sets the display order of a plurality of externally processed images (thumbnails) according to the transmission order of transmitting the radiation images to the external processing apparatuses 800.

According to this configuration, a plurality of externally processed images (thumbnails) is arranged in order and displayed according to the transmission order of transmitting the radiation images to the external processing apparatuses 800. Thus, the user can efficiently perform the work of confirming an externally processed image. This can prevent a decrease in the operability for the user and the incorrect recognition of an image.

An embodiment obtained by combining the present exemplary embodiment and at least one of the first to fifth exemplary embodiments is also included in the present disclosure.

The present disclosure includes an embodiment in which a configuration including the overall control unit 120, the radiation generating apparatus control unit 130, the operation unit 140, and the display control unit 150 except for the radiation detection unit 110 in the configuration of the radiation imaging apparatus 100 illustrated in FIG. 1 is an "information processing apparatus".

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. An information processing apparatus comprising:
an obtaining unit configured to obtain, from at least one external processing apparatus, a plurality of processed images obtained by the at least one external processing apparatus processing a plurality of radiation images; and
a control unit configured to perform control to, according to a display order corresponding to a transmission order of transmitting of the plurality of radiation images to the at least one external processing apparatus, display the plurality of processed images on a display unit.

2. The information processing apparatus according to claim 1, further comprising a setting unit configured to set the display order,
wherein the setting unit sets the display order according to the transmission order and a type of a processing content of the at least one external processing apparatus.

3. The information processing apparatus according to claim 1, further comprising:
a setting unit configured to set the display order; and
a storage unit configured to store information indicating the display order determined according to the transmission order, types of a plurality of external processing apparatuses and types of processing contents of the plurality of external processing apparatuses,
wherein the obtaining unit obtains the plurality of processed images from the plurality of external processing apparatuses, and
wherein the setting unit sets the display order based on information indicating the display order stored in the storage unit.

4. The information processing apparatus according to claim 1, further comprising a setting unit configured to set the display order,
wherein the obtaining unit obtains the plurality of processed images from a plurality of external processing apparatuses, and
wherein the setting unit sets a position in the display order of the processed image obtained by a prioritized external processing apparatus among the plurality of external processing apparatuses before a position in the display order of the processed image obtained by another external processing apparatus except for the prioritized external processing apparatus among the plurality of external processing apparatuses.

5. The information processing apparatus according to claim 1, further comprising a setting unit configured to set the display order,
wherein the setting unit sets the display order according to the transmission order and whether the radiation image is already output to an output destination different from the at least one external processing apparatus.

6. The information processing apparatus according to claim 5, wherein the setting unit sets a position in the display order of the processed image of which an original image is the radiation image that is not already output before a position in the display order of the processed image of which an original image is the radiation image that is already output.

7. The information processing apparatus according to claim 1, further comprising a setting unit configured to set the display order,
wherein the setting unit sets the display order according to the transmission order and whether the radiation image is already rejected or deleted.

8. The information processing apparatus according to claim 7, wherein the setting unit sets a position in the display order of the processed image of which an original image is the radiation image that is already rejected or deleted after a position in the display order of the processed image of which an original image is the radiation image that is not already rejected or deleted.

9. The information processing apparatus according to claim 1, wherein a setting unit sets a position in the display order of the processed image of which an original image is the radiation image transmitted earlier among the plurality of radiation images before a position in the display order of the processed image of which an original image is the radiation image transmitted later among the plurality of radiation images.

10. The information processing apparatus according to claim 1, further comprising a setting unit configured to set the display order,
wherein the setting unit sets the display order so that the processed image obtained by processing each of a plurality of radiation images is located adjacent to the radiation image.

11. The information processing apparatus according to claim 1, further comprising a setting unit configured to set the display order,
wherein the setting unit sets the display order with respect to each series including a group of images related to each other.

12. The information processing apparatus according to claim 1, wherein the control unit performs control to display a thumbnail of the processed image as the processed image on the display unit.

13. A radiation imaging system comprising:
a detection unit configured to detect radiation; and
the information processing apparatus according to claim 1, communicably connected to the detection unit and communicably connected to the at least one external processing apparatus.

14. An information processing apparatus comprising:
an obtaining unit configured to obtain, from a plurality of external processing apparatus, a plurality of processed images obtained by the plurality of external processing apparatuses processing a plurality of radiation images, and
a control unit configured to perform control to, according to types of the plurality of external processing apparatuses, display the plurality of processed images on a display unit.

15. An information processing method comprising:
obtaining, from at least one external processing apparatus, acquiring a plurality of processed obtained by the at least one external processing apparatus processing a plurality of radiation images; and
performing control to, according to a display order corresponding to a transmission order of transmitting of the plurality of radiation images to the at least one external processing apparatus, display the plurality of processed images on a display unit.

16. A non-transitory computer-readable storage medium storing a program for causing a computer to execute an information processing method comprising:
obtaining, from at least one external processing apparatus, a plurality of processed images obtained by the at least one external processing apparatus processing a plurality of radiation images; and
performing control to, according to a display order corresponding to a transmission order of transmitting of the plurality of radiation images to the at least one external processing apparatus, display the plurality of processed images on a display unit.

* * * * *